United States Patent
Jeong

(10) Patent No.: US 9,089,352 B2
(45) Date of Patent: Jul. 28, 2015

(54) SURGICAL ROBOT SYSTEM HAVING TOOL FOR MINIMALLY INVASIVE SURGERY

(76) Inventor: Chang Wook Jeong, Seoul (KR)

( * ) Notice: Subject to any disclaimer, the term of this patent is extended or adjusted under 35 U.S.C. 154(b) by 736 days.

(21) Appl. No.: 13/127,009

(22) PCT Filed: Oct. 30, 2009

(86) PCT No.: PCT/KR2009/006333
§ 371 (c)(1), (2), (4) Date: Apr. 29, 2011

(87) PCT Pub. No.: WO2010/050771
PCT Pub. Date: May 6, 2010

(65) Prior Publication Data
US 2011/0213384 A1 Sep. 1, 2011

(30) Foreign Application Priority Data
Oct. 31, 2008 (KR) ........................ 10-2008-0108103

(51) Int. Cl.
*A61B 17/00* (2006.01)
*A61B 19/00* (2006.01)
*A61B 17/29* (2006.01)

(52) U.S. Cl.
CPC ... *A61B 19/2203* (2013.01); *A61B 2017/00973* (2013.01); *A61B 2017/2927* (2013.01); *A61B 2019/2242* (2013.01); *A61B 2019/2276* (2013.01)

(58) Field of Classification Search
CPC ........... A61B 19/2203; A61B 17/3423; A61B 2017/00283; A61B 2017/00973; A61B 2017/2908; A61B 2017/2927; A61B 2019/2223; A61B 2019/2234; A61B 2019/2242; A61B 2019/2276; A61B 2019/5227; B25J 9/0018; B25J 9/06
USPC ....................................... 606/1, 130; 600/104
See application file for complete search history.

(56) References Cited

U.S. PATENT DOCUMENTS

| | | | |
|---|---|---|---|
| 4,853,874 A | 8/1989 | Iwamoto et al. | |
| 5,710,870 A * | 1/1998 | Ohm et al. | 700/263 |
| 5,779,623 A | 7/1998 | Bonnell | |
| 5,807,377 A * | 9/1998 | Madhani et al. | 606/1 |
| 5,820,623 A * | 10/1998 | Ng | 606/1 |
| 5,931,832 A * | 8/1999 | Jensen | 606/1 |
| 6,102,850 A | 8/2000 | Wang et al. | |
| 6,197,017 B1 * | 3/2001 | Brock et al. | 606/1 |
| 6,331,181 B1 | 12/2001 | Tierney et al. | |
| 6,676,684 B1 * | 1/2004 | Morley et al. | 606/205 |
| 6,786,896 B1 | 9/2004 | Madhani et al. | |
| 6,905,491 B1 | 6/2005 | Wang et al. | |
| 2008/0071291 A1 | 3/2008 | Duval et al. | |

* cited by examiner

FOREIGN PATENT DOCUMENTS

JP 2006061364 A 3/2006
KR 1020080027224 A 3/2008

OTHER PUBLICATIONS

International Search Report for PCT Application PCT/KR2009/006333. Korean Intellectual Property Office. Jun. 10, 2010.

*Primary Examiner* — Julian W Woo
(74) *Attorney, Agent, or Firm* — Mayer Brown LLP

(57) ABSTRACT

The present invention relates to a surgical robot system having a tool for minimally invasive surgery. More specifically, the present invention relates to a surgical robot system that helps a user such as a surgeon control the tool for minimally invasive surgery in a dexterous and convenient manner.

21 Claims, 36 Drawing Sheets

SURGICAL ROBOT SYSTEM HAVING TOOL FOR MINIMALLY INVASIVE SURGERY

PRIORITY

The present application claims priority under 35 U.S.C. §371 to PCT Application PCT/KR2009/006333, filed on Oct. 30, 2009, which claims priority to Korean Patent Application No. 10-2008-0108103, filed on Oct. 31, 2008, the disclosures of which are hereby incorporated by reference in their entireties.

FIELD OF THE INVENTION

The present invention relates to a surgical robot system having a tool for minimally invasive surgery. More specifically, the present invention relates to a surgical robot system that helps a user such as a surgeon control the tool for minimally invasive surgery in a dexterous and convenient manner.

BACKGROUND OF THE INVENTION

Minimally invasive surgery is a surgical approach that involves use of instruments inserted through several tiny incision openings to perform a surgery causing minimal tissue trauma.

This minimally invasive surgery relatively reduces changes in metabolism of the patient in the period of post-surgical care, so it is beneficial to rapid recovery of the patient. Therefore, using such minimally invasive surgery shortens length of a hospital stay of the patient after the surgery and allows patients to return to normal physical activities more quickly. In addition, minimally invasive surgery causes less pain and reduces scar to patients after surgery.

The most general form of the minimally invasive surgery is endoscopy. Among them, a laparoscopy that involves minimally-invasive inspection and operation inside abdominal cavity is known as the most general form of endoscopy. To operate the standard laparoscopic surgery, an abdomen of the patient is insufflated with gas, and small incisions (about ½ inch or less) are formed for use as an entrance of a tool for the laparoscopic surgery, through which a trocar is inserted. In general, laparoscopic surgical tools include a laparoscope (for observation of a surgical site) and other working tools. Here, the working tools are similar in structure to the conventional tools used for small incision surgery, except that the end effector or working end of each tool is separated from its handle by an elongated shaft. For instance, working tools may include a clamp, a grasper, scissors, a stapler, a needle holder, and so forth. To perform the surgery, a user, such as a surgeon, puts the working tool into a surgical site through the trocar, and manipulates it from the outside of abdominal cavity. Then, the surgeon monitors the procedure of the surgery through a monitor that displays the image of the surgical site that is taken by the laparoscope. The endoscopic approach similar to this is broadly used in retroperitoneoscopy, pelviscopy, arthroscopy, cisternoscopy, sinuscopy, hysteroscopy, nephroscopy, cystoscopy, urethroscopy, pyeloscopy, and so on.

Although this minimally invasive surgery has a number of advantages, it has shortcomings in the difficulty of approaching the conventional minimally invasive surgical tools to a surgical site and the inconvenient or complicate manipulation of such tools because of an end effector connected to a rigid and long shaft. As attempts to solve the above problems, the present inventor has devised a novel tool for minimally invasive surgery as described in Korean Patent Application Nos. 2008-51248, 2008-61894, 2008-79126 and 2008-90560 filed prior to this application, the contents of which are herein incorporated by reference in their entirety.

In particular, among these applications, the minimally invasive surgical tools disclosed in Korean Patent Application Nos. 2008-79126 and 2008-90560 are very useful in a case where only a single incision is formed in a patient's body to perform surgery. Accordingly, the inventor devised a surgical robot system having a tool for minimally invasive surgery described in at least one of the prior applications or a surgical robotic system which adopts the principles of the tool.

SUMMARY OF THE INVENTION

The present invention is directed to solve all of the problems mentioned above.

It is an object of the present invention to provide a surgical robot system suitable for use with a tool for carrying out a minimally invasive surgery in a dexterous and convenient manner.

Another object of the present invention is to provide a surgical robot system for enabling a user to perform remote surgery even if a patient to be operated on is far away in a physically different location.

Still another object of the present invention is to provide a surgical robot system for helping a user perform a minimally invasive surgery within a relatively short period of time using relatively low energy.

In accordance with one aspect of the present invention, there is provided a Surgical robot system comprising, a plurality of robot arms, and a surgery actuator, wherein the surgery actuator is controlled in a pitch direction and/or in a yaw direction by at least one of the plurality of robot arms, wherein the surgery actuator comprises at least one tool for minimally invasive surgery, wherein the at least one tool for minimally invasive surgery comprises a main shaft, a first actuating shaft, a second actuating shaft, an end effector and a handling part, and wherein the handling part controls the first actuating shaft, the second actuating shaft and the end effector.

BRIEF DESCRIPTION OF THE DRAWINGS

The above and other objects and features of the present invention will become apparent from the following description of preferred embodiments, given in conjunction with the accompanying drawings, in which.

DETAILED DESCRIPTION OF THE PREFERRED EMBODIMENT

Figure 1:
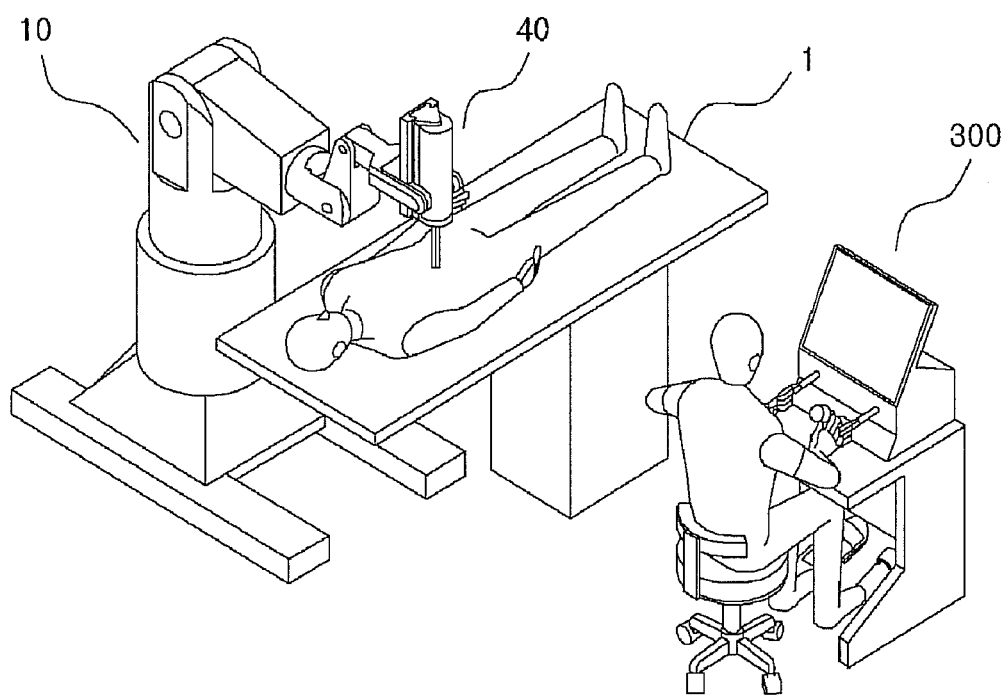
FIG. 1 shows an overall configuration of a surgical robot system in accordance with one embodiment of the present invention.

In the following detailed description, reference is made to the accompanying drawings that show, by way of illustration, specific embodiments in which the invention may be practiced. These embodiments are described in sufficient detail to enable those skilled in the art to practice the invention. It is to be understood that the various embodiments of the invention, although different, are not necessarily mutually exclusive. For example, a particular feature, structure, or characteristic described herein in connection with one embodiment may be implemented within other embodiments without departing from the spirit and scope of the present invention. Also, it is to be understood that the positions or arrangements of individual elements in the embodiment may be changed without separating the spirit and scope of the present invention. The following detailed description is, therefore, not to be taken in a limiting sense, and the scope of the present invention is defined only by the appended claims that should be appropriately interpreted along with the full range of equivalents to which the claims are entitled. In the drawings, like reference numerals identify like or similar elements or functions through the several views.

Hereinafter, preferred embodiments of the present invention will be explained in detail with reference to the accompanying drawing so that those skilled in the art can easily practice the invention.

Configuration of Surgical Robot System

FIG. 1 shows an overall configuration of a surgical robot system in accordance with one embodiment of the present invention, in which the surgical robot system includes an actuation robot 10 and a surgery actuator 40 both being associated with performing surgery on a patient on an operating table 1, and a main control part 300 for controlling the actuation robot 10 and the surgery actuator 40 in response to user manipulation. Handling of adjusting levers, joysticks and pedals by the main control part 300 is transformed to an electric signal and transmitted to the actuation robot 10 and/or the surgery actuator 40, and a device like an electric motor/hydraulic cylinder drives and controls the actuation robot 10 and/or the surgery actuator 40 based on a transmitted signal.

More details on prior art techniques of the configuration of the main control part 300 can be found in U.S. Pat. No. 4,853,874 entitled "Master-slave Manipulators with Scaling"; U.S. Pat. No. 5,779,623 entitled "Positioner for Medical Instruments"; and U.S. Pat. No. 6,102,850 entitled "Medical Robotic System". It should be noted, however, that the mention of such prior art techniques does not intend to limit the configuration of the main control part 300 of the present invention solely to the application of them.

Figure 2:
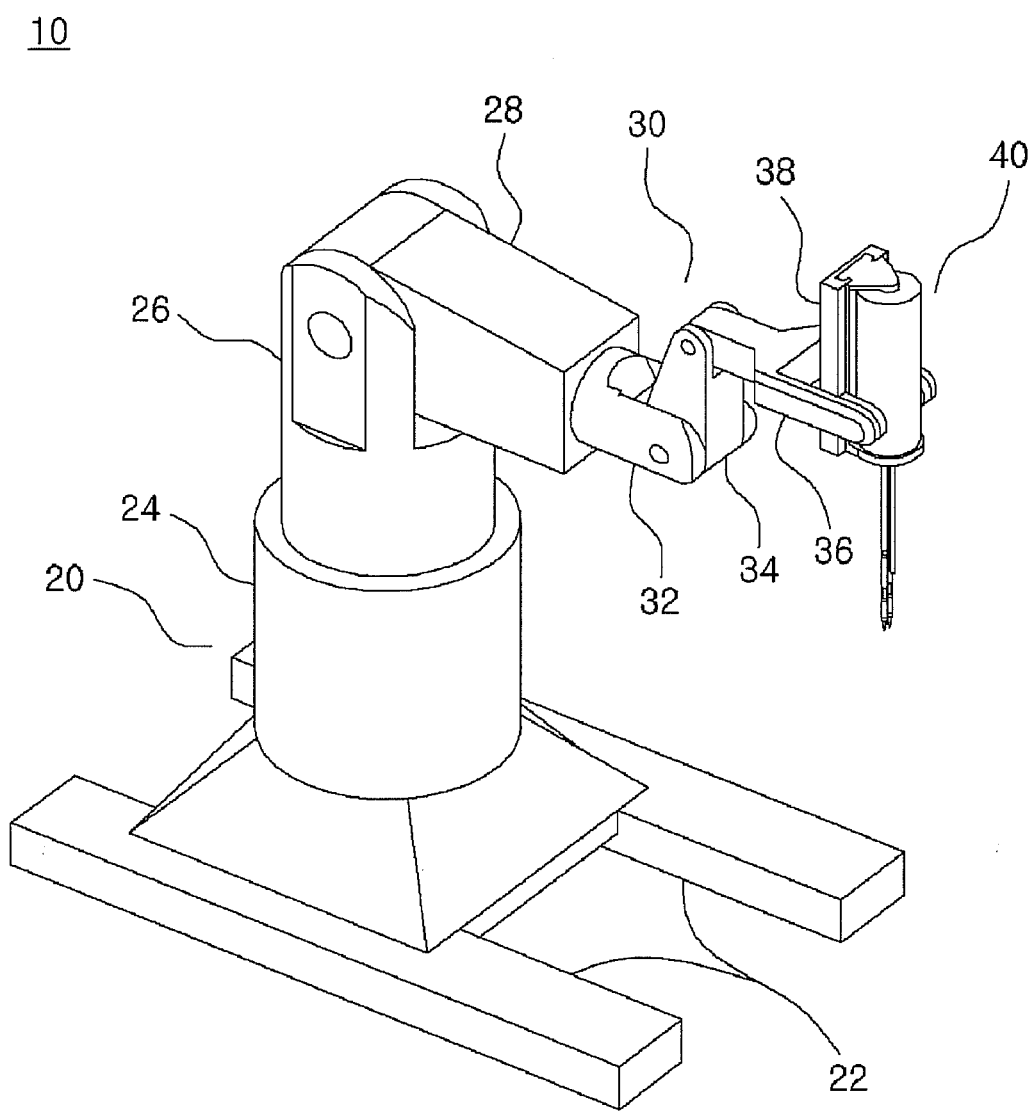
FIG. 2 is a perspective view showing an overall configuration of an actuation robot included in the surgical robot system in accordance with one embodiment of the present invention.

FIG. 2 is a perspective view showing an overall configuration of the actuation robot 10 included in the surgical robot system in accordance with one embodiment of the present invention, in which the actuation robot 10 is composed of a base 20 (which may include a horizontal support 22, a vertical support 24, a vertical arm 26 and a horizontal arm 28) for supporting all, and a robot arm 30 (which may include first through fourth robot arms 32, 34, 36 and 38) connected to the base 20 and making surgical motions in response to user manipulation.

The base 20 is preferably configured to prevent the entire actuation robot 10 against vibrations caused by external forces so as to make surgery proceed as smooth as possible. To this end, the base 20 includes a horizontal support 22 and a vertical support 24 made of high load-bearing materials, and thus can stand firm on the ground.

Moreover, the base 20 includes a vertical arm 26 operating in a surge direction (i.e., forward and backward motions in an axis direction and in a roll direction, and a horizontal arm 28 operating in a pitch direction. The vertical arm 26 and the horizontal arm 28 can control positions of robot arms (to be described later).

The robot arm 30 is connected to the surgery actuator 40, with the surgery actuator 40 having an endoscope and/or tools for minimally invasive surgery. The robot arm 30 can be configured to operate in a surge direction, a pitch direction and/or in a roll direction, in response to user manipulation. More details on this will be provided below.

Figure 3:
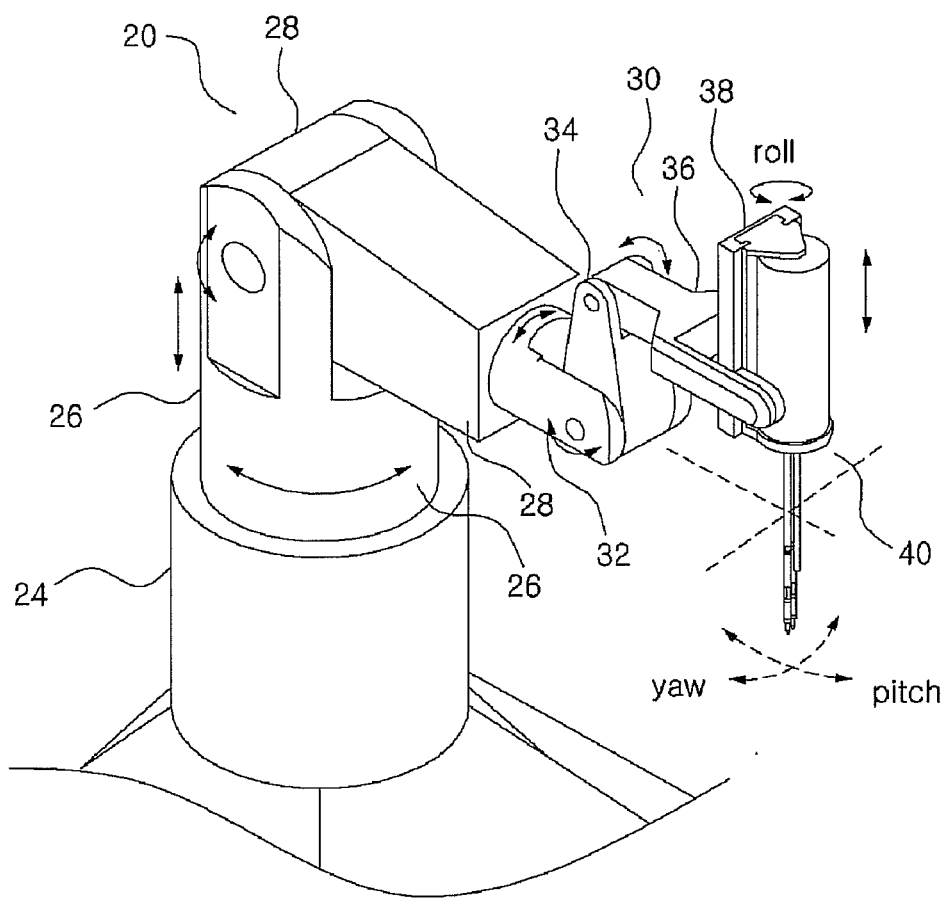
FIGS. 3 and 4 show the configuration and operations of robot arms in accordance with one embodiment of the present invention.
Figure 4:
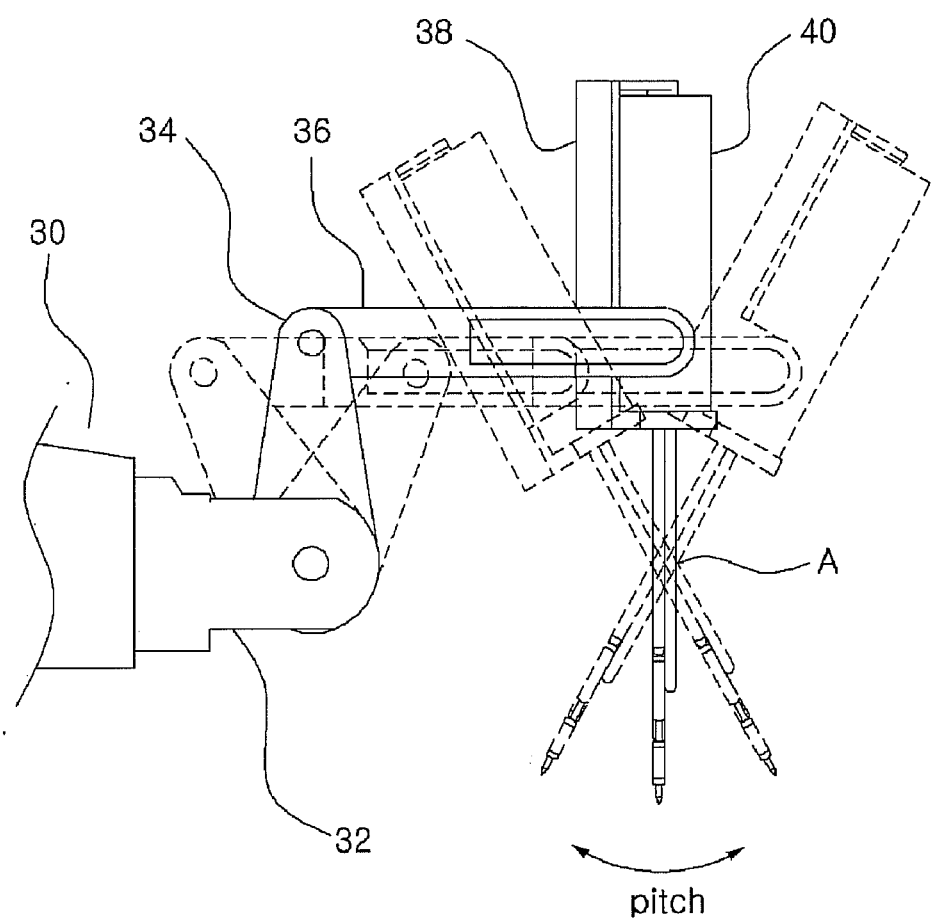

FIGS. 3 and 4 show the configuration and operations of robot arms in accordance with one embodiment of the present invention. As illustrated in FIGS. 3 and 4, the robot arm 30 connected to the base 20 is constituted by first through fourth robot arms 32, 34, 36 and 38.

Figure 5:
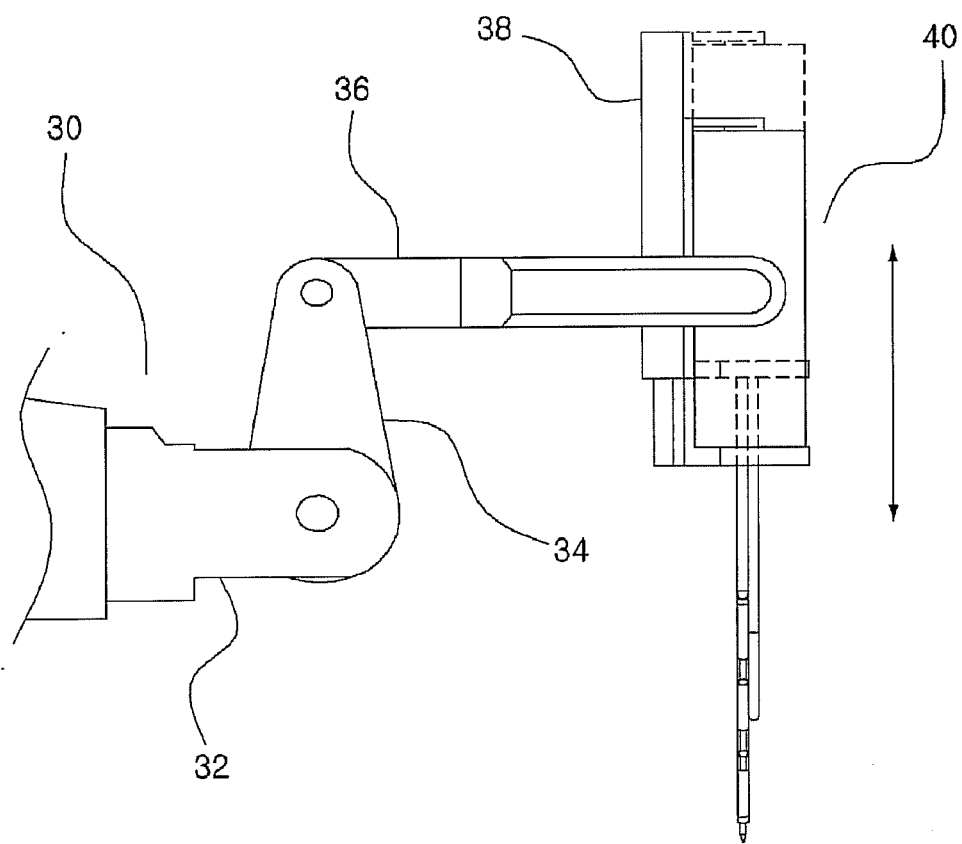
FIG. 5 shows that a surgery actuator in accordance with one embodiment of the present invention operates in a surge direction in parallel to the vertical axis of a fourth robot arm.

The first robot arm 32 operates in a roll direction with respect to the horizontal arm 28 (this can cause the surgery actuator 40 to operate in a yaw direction), as shown. The second robot arm 34 operates in a pitch direction with respect to the first robot arm 32 (this can cause the surgery actuator 40 to operate in a pitch direction). Here, as illustrated in FIG. 4, the third robot arm 34 preferably operates in parallel to the vertical axis of the first robot arm 32, such that an operational direction of the fourth robot arm 38 in the pitch direction is substantially identical to an operational direction of the second robot arm 34 in the pitch direction. Referring to FIG. 4, the surgery actuator 40 operates in the pitch direction with respect to an intersection (i.e., 'A' portion) between the vertical axis of the first robot arm 32 and the vertical axis of the surgery actuator 40. FIG. 5 shows that the surgery actuator 40 in accordance with one embodiment of the present invention operates in the surge direction in parallel to the vertical axis of the fourth robot arm 38. Once the surgery actuator 40 is properly positioned by the first through fourth robot arms 32, 34, 36 and 38, it can operate in the surge and roll directions independently.

Figure 6:
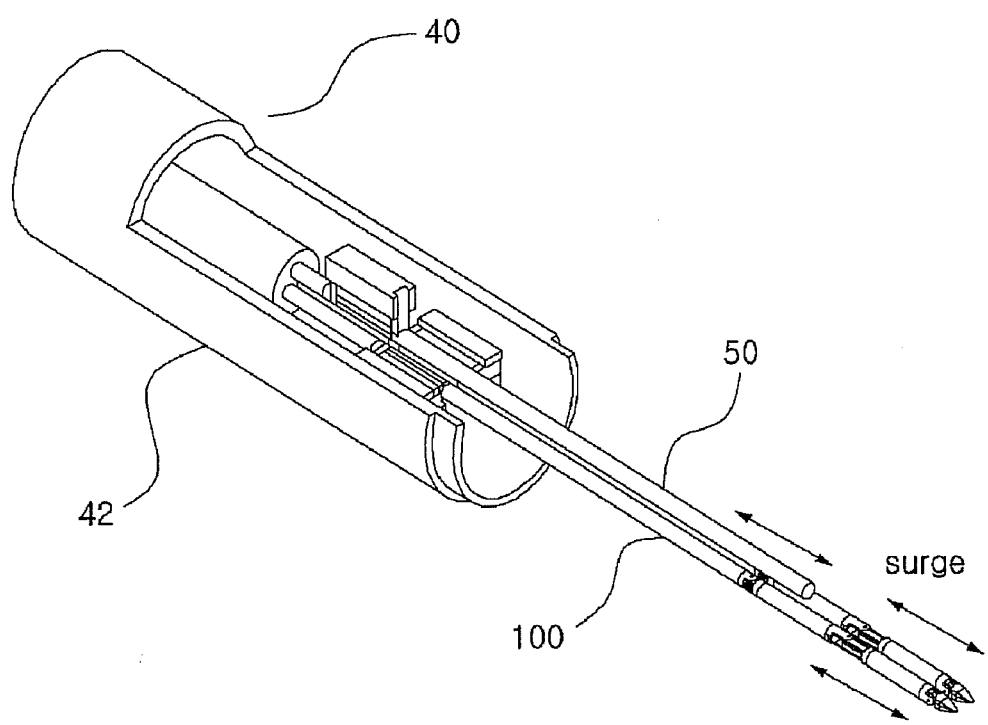
FIGS. 6 and 7 show a detailed configuration of the surgery actuator in accordance with one embodiment of the present invention and actuations of an endoscope and a tool for minimally invasive surgery with respect to the surgery actuator thereof.
Figure 7:
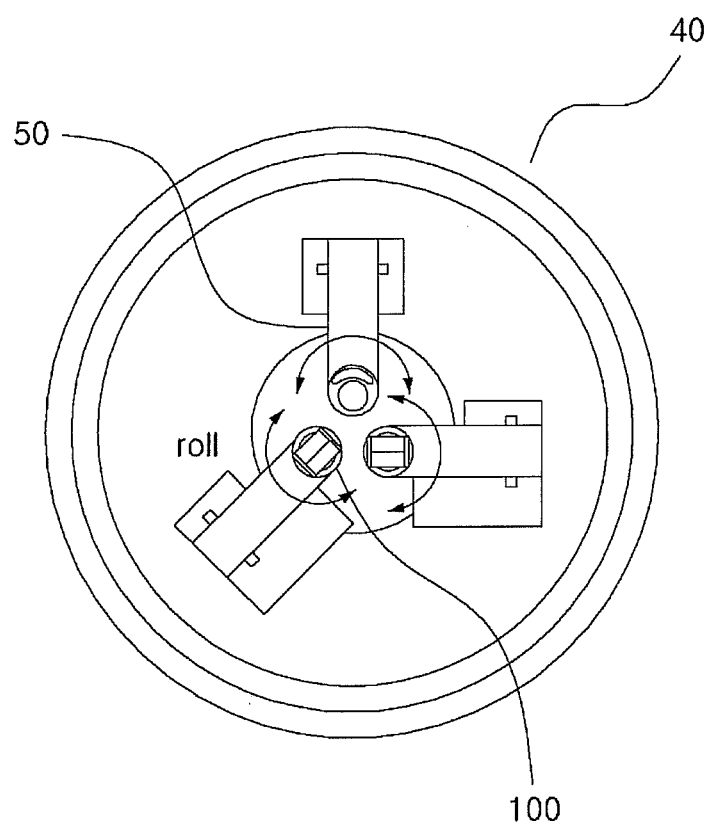

FIGS. 6 and 7 show a detailed configuration of the surgery actuator 40 in accordance with one embodiment of the present invention. As illustrated in FIGS. 6 and 7, an endoscope 50 and tools 100 for minimally invasive surgery are formed in a bundle within a cylindrical body 42 having a preset length for the surgery actuator 40. The endoscope 50 and the tool 100 for minimally invasive surgery are driven by a drive unit (not shown) that is disposed at the surgical actuator 40, in response to user manipulation, so as to operate individually in a surge direction and in a roll direction.

Figure 8:
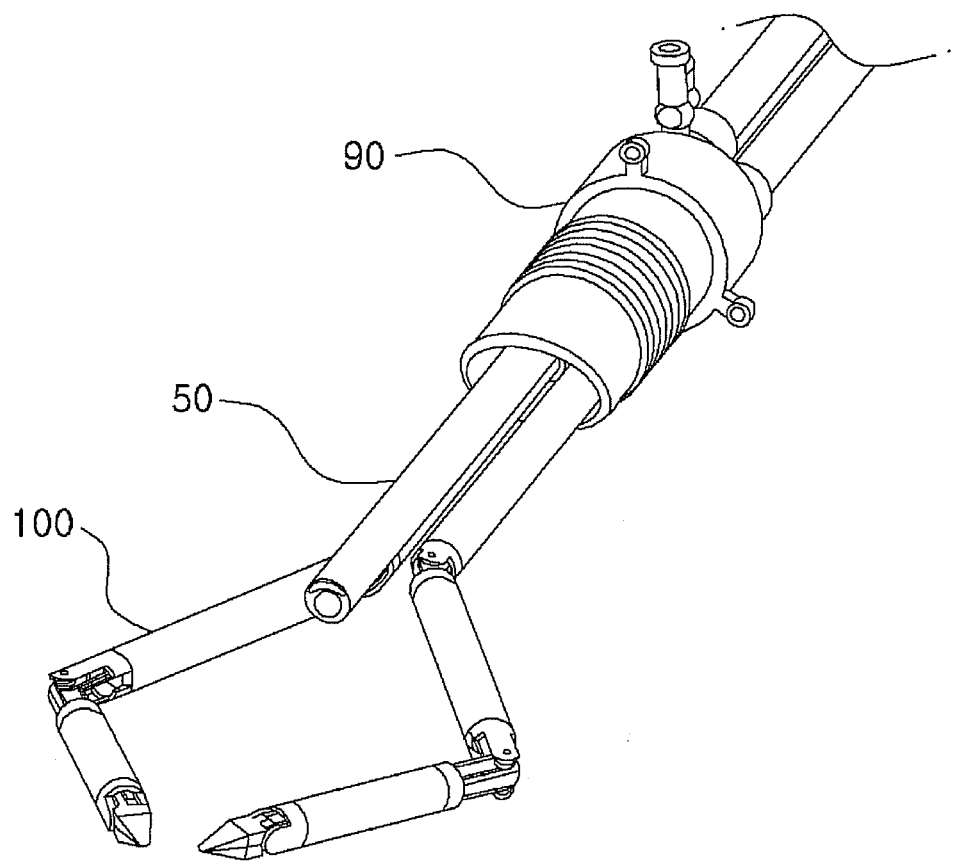
FIGS. 8 and 9 show examples where the endoscope and the tool for minimally invasive surgery in accordance with one embodiment of the present invention are formed in a bundle.
Figure 9:
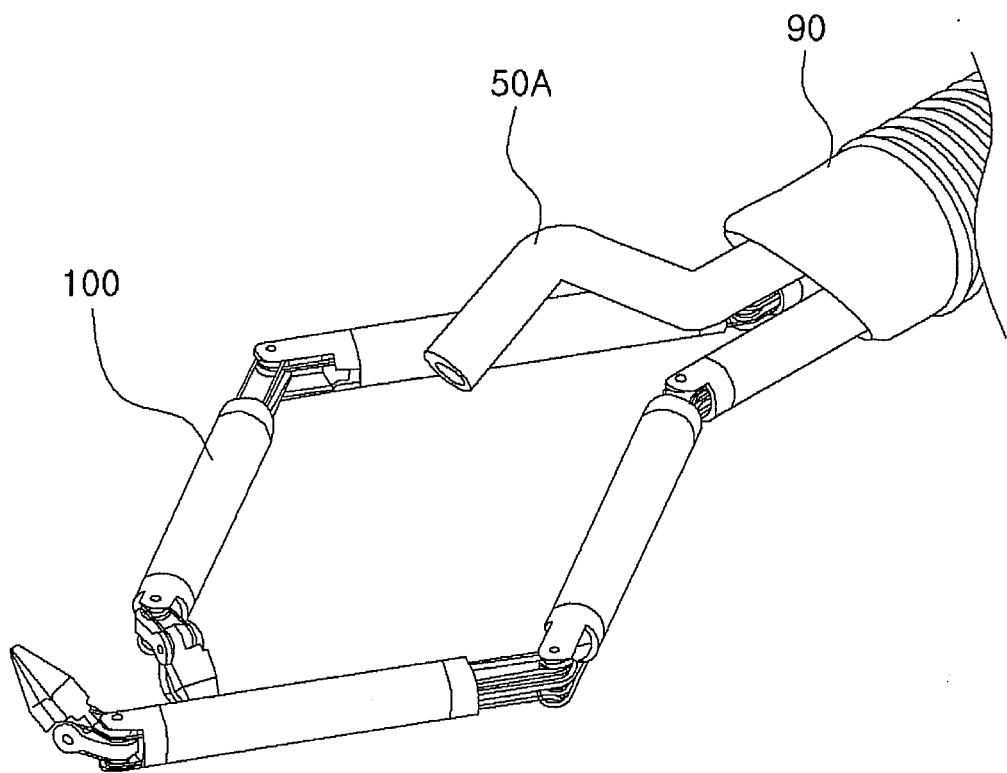

Turning now to FIGS. 8 and 9, there are shown examples where the endoscopes 50 and 50A and the tool 100 for minimally invasive surgery are formed in a bundle in accordance with one embodiment of the present invention. Preferably, the endoscopes 50 and 50A and the tool 100 for minimally invasive surgery are positioned within the surgery actuator 40 in form of a bundle (more preferably, the endoscopes 50 and 50A and the tool 100 for minimally invasive surgery may be inserted into a patient's body in form of a bundle). To this end, a surgical port 90 as shown in FIG. 8 may be utilized. More information on the surgical port 90 can be found in the detailed description of specification for Korean Patent Application No. 2008-99872 filed by the same applicant, the contents of which are incorporated herein by reference in its entirety. The endoscopes 50 and 50A may have a linear form as illustrated in FIG. 8, or endoscopes with diverse ranges of bending such as joints or freely bending flexible endoscopes as illustrated in FIG. 9 and described in Korean Patent Application Nos. 2008-51248, 2008-61894, 2008-79126 and 2008-90560 may also be used.

Figure 10:
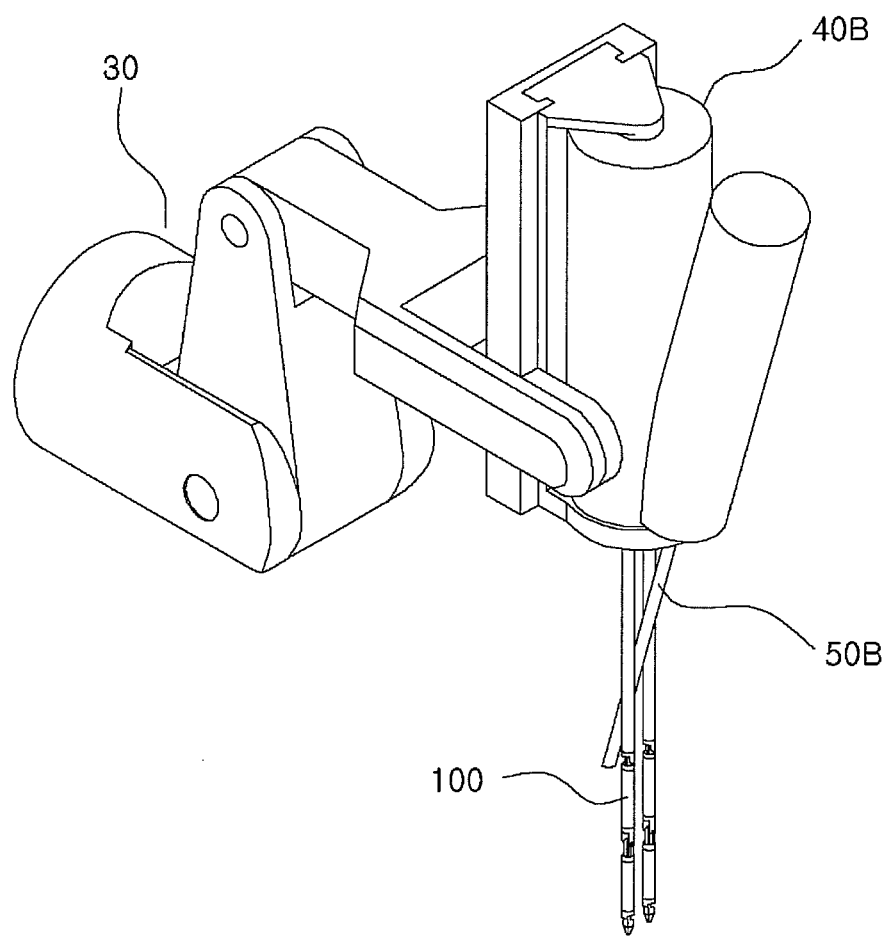
FIG. 10 shows an example of how the endoscope in accordance with one embodiment of the present invention is positioned.

Meanwhile, depending on the kind of surgery, it is sometimes better for a user to see an operation field of the patient at an oblique angle from above. Therefore, to enable the user (i.e., surgeon) to see the operation field of the patient nearly identically as seeing with the naked eye, the endoscope 50B may be built at a preset oblique angle with respect to the tool 100 for minimally invasive surgery as illustrated in FIG. 10. The oblique angle can be set depending on the user's needs.

Among the endoscopes positioned within the surgery actuator 40, the endoscope 50A having an articulation function may be connected with a drive roller (to be described later), but may not be connected as well.

Figure 11:
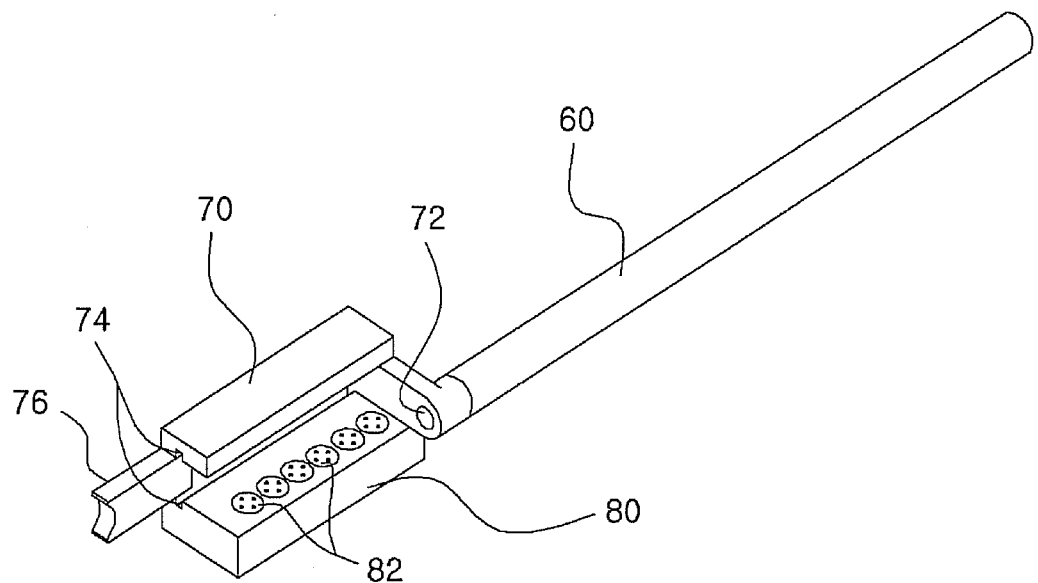
FIG. 11 shows the configuration of a subarm and a drive part in accordance with one embodiment of the present invention.

Now, details on FIG. 11 will be given. FIG. 11 shows the configuration of a subarm 60 and a drive part 80 in accordance with one embodiment of the present invention. As illustrated in FIG. 11, the tool 100 for minimally invasive surgery is connected to one end (the end on the side of the drive part 80) of the subarm 60 in form of a linear tube. A mount 70 is positioned at one end of the subarm 60, with the mount 70 including a groove 72, a linear groove 74, and a cover 76. Additionally, the drive part 80, which includes plural drive rollers 82 for driving a handling part (to be described later) used for the control of the operation of the tool 100 for minimally invasive surgery, can be connected. The drive rollers 82 may be driven by drive units well-known in the prior art.

Figure 12:
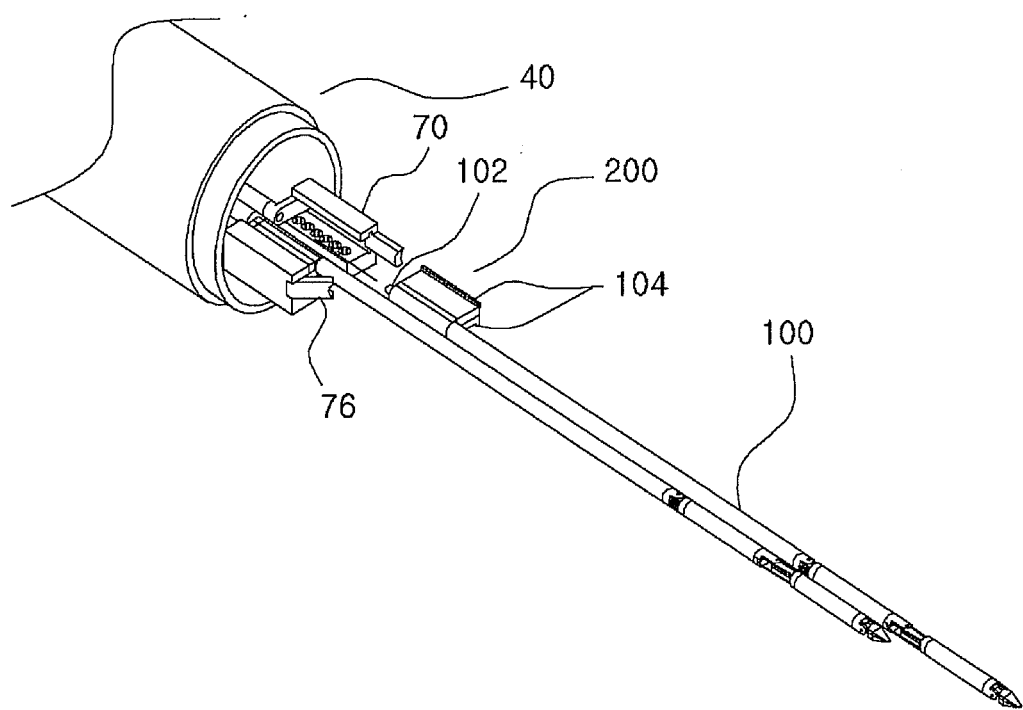
FIG. 12 shows an example of how a tool for minimally invasive surgery is positioned in the surgery actuator in accordance with one embodiment of the present invention.
Figure 13:
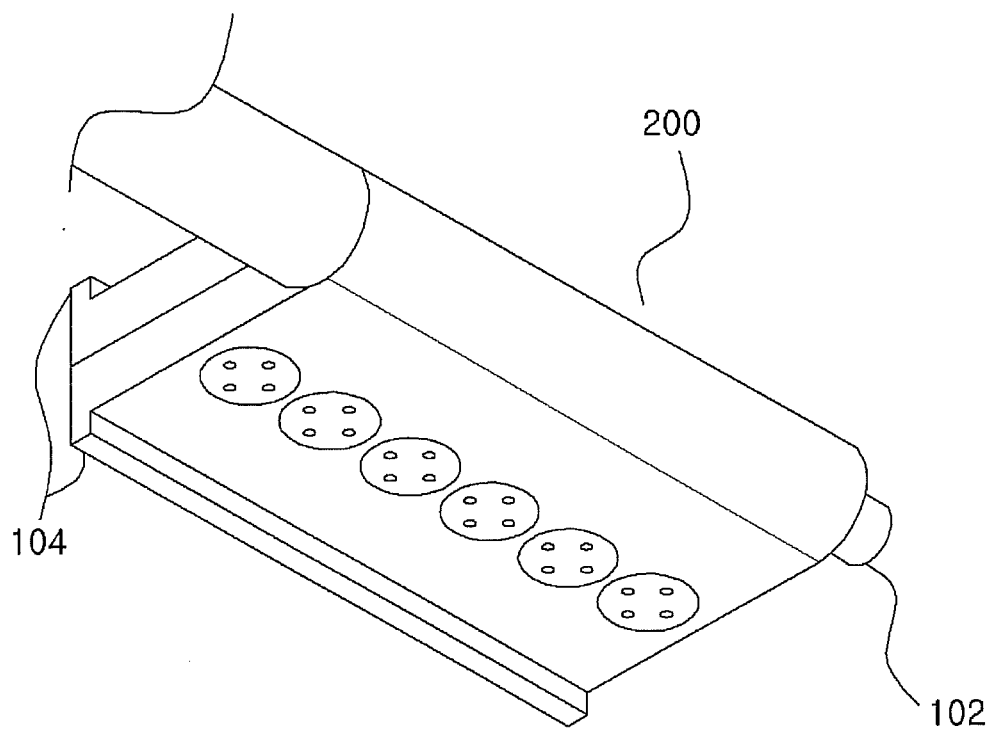
FIG. 13 is a bottom perspective view of a handling part for driving the tool for minimally invasive surgery in accordance with one embodiment of the present invention.
Figure 14:
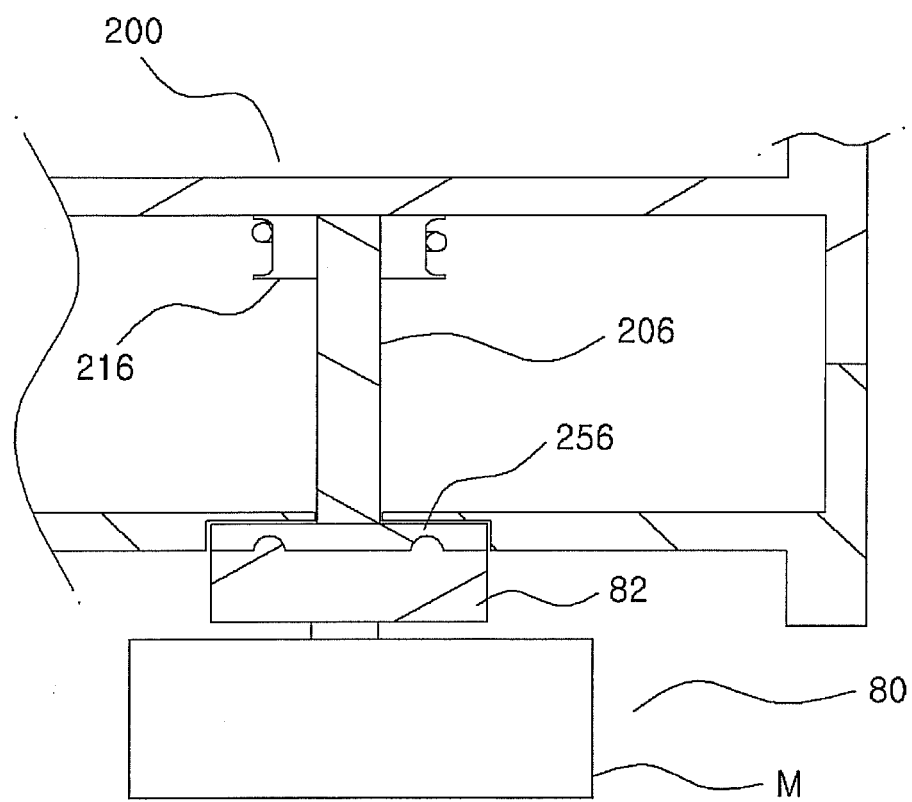
FIG. 14 is a cross-sectional view showing how a drive part and a handling part are connected in accordance with one embodiment of the present invention.

FIG. 12 shows an example of how the tool 100 for minimally invasive surgery is positioned within the surgery actuator 40 in accordance with one embodiment of the present invention, FIG. 13 is a bottom perspective view of the handling part 200 for driving of the tool 100 for minimally invasive surgery, and FIG. 14 is a cross-sectional view showing how the drive part 80 and the handling part 200 are connected. The following is a more detailed explanation about disposition of the tool 100 for minimally invasive surgery, with reference to FIG. 11 and FIGS. 12 through 14.

As noted earlier, the drive part 80 preferably including the plural drive rollers 82 is positioned at the end of the subarm 60. The handling part 200 for controlling the tool 100 for minimally invasive surgery may be placed contiguous with the drive part 80. Moreover, the mount 70 includes a groove 72 and a linear groove 74, and the handling part 200 includes a protrusion 102 and a linear protrusion 104 to join to each other. After the protrusion 102 and the linear protrusion 104 are fitted into the groove 72 and the linear groove 74, respectively, the cover 76 is placed over them.

With the mount 70 and the handling part 200 being joined to each other as described above, it is sometimes necessary to transfer a rotational motion of the drive rollers 82 of the drive part 80 to the tool 100 for minimally invasive surgery via a drive pulley (to be described later) of the handling part 200. To this end, as illustrated in FIG. 14, a connection roller 256 is positioned at one end of a drive shaft 206 (6$^{th}$ drive shaft 206 as will be described later) constituting the handling part 200 to be exposed outside of the handling part 200, and then the connection roller 256 is brought into contact with one drive roller 82 of the drive part 80. By doing so, the drive pulley 216 is operationally coupled in its rotation with the rotational motions of the drive roller 82 and the connection roller 256. To make the power transfer proceed smoothly from the drive roller 82 to the connection roller 256, a contact surface between the drive roller 82 and the connection roller 256 may have a groove and a projection. Although the joint between the drive roller 82 close to the 6$^{th}$ drive shaft 206 out of many drive shafts that constitute the handling part 200 and the connection roller 256 has been explained, such joint or link can equally be made around other drive shafts that constitute the handling part 200.

For information, the tool 100 for minimally invasive surgery in accordance with one embodiment of the present invention described in the aforementioned Korean Patent Application No. 2008-90560 is illustrated in FIG. 12, but other tools for minimally invasive surgery, namely, the surgical tools according to each embodiment in the other Korean Patent Applications mentioned above, may be positioned in diverse and creative manner. That is to say, the selection of a tool for minimally invasive surgery used for the surgery actuator 40 can be made voluntarily by the user.

Hereinafter, various embodiments of the present invention will be described, with a primary focus on the configuration of the handling part 200 that allows the tool 100 for minimally invasive surgery to be positioned and operate within the surgery actuator 40.

Configurations of Tool for Minimally Invasive Surgery and Handling Part

Embodiment I

Figure 15:
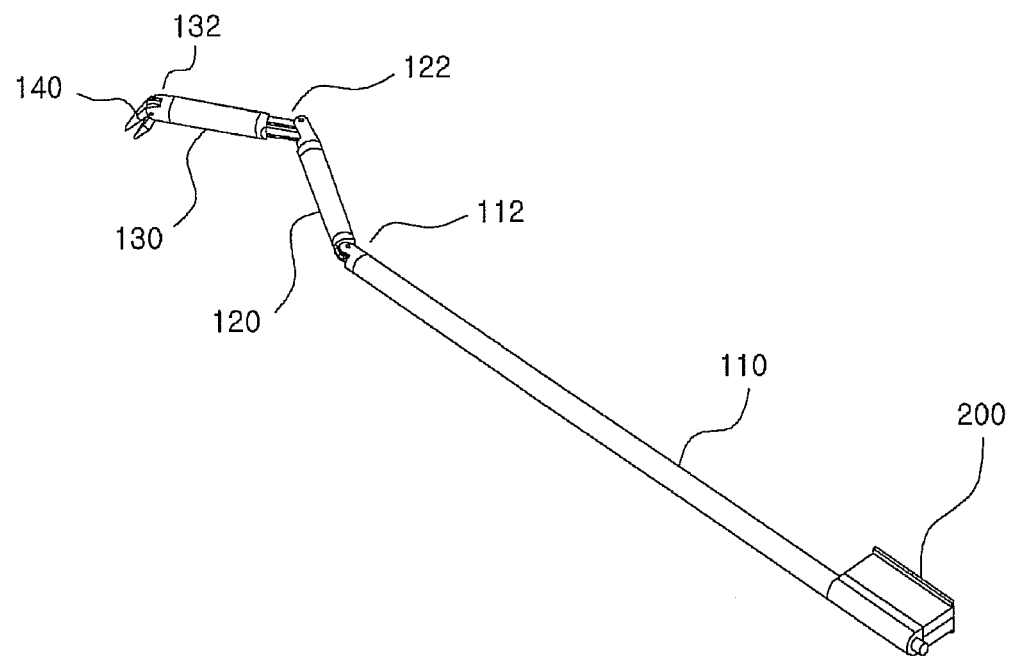
FIG. 15 is a perspective view showing an example of a tool for minimally invasive surgery used for the present invention.

FIG. 15 is a perspective view showing an example of the tool 100 for minimally invasive surgery used for the present invention.

The tool 100 for minimally invasive surgery includes a shaft 110 (i.e., main shaft), first and second actuating shafts 120 and 130 connected to one end of the main shaft 110 through first and second yaw actuating parts 112 and 122, respectively, and an end effector 140 connected to the end of the second actuating shaft 130 with a pitch actuating part 132. Also, a handling part 200 is positioned at the other end of the shaft 110 to actuate the first and second actuating shafts 120 and 130, and to actuate the end effector 140.

More details on the configurations of the first and second actuating shafts 120 and 130 extendedly connected to one end of the shaft 110, the end effector 140 and yaw cable YC connected thereto, and first and second pitch cables PC1 and PC2 can be found in the first embodiment of the detailed description for the invention disclosed in Korean Patent Application No. 2008-90560, so any details on those configurations will be omitted here.

The configuration of the handling part 200 will now be discussed in more detail.

Figure 16:
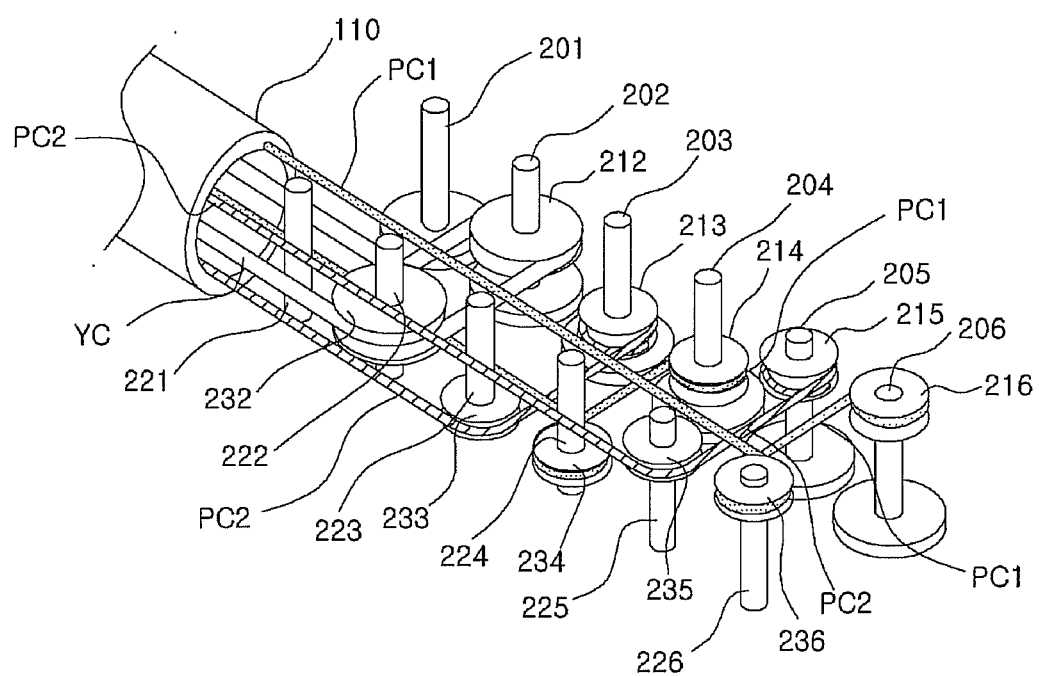
FIGS. 16 and 17 are perspective views showing the configuration of a handling part in accordance with a first embodiment of the present invention.
Figure 17:
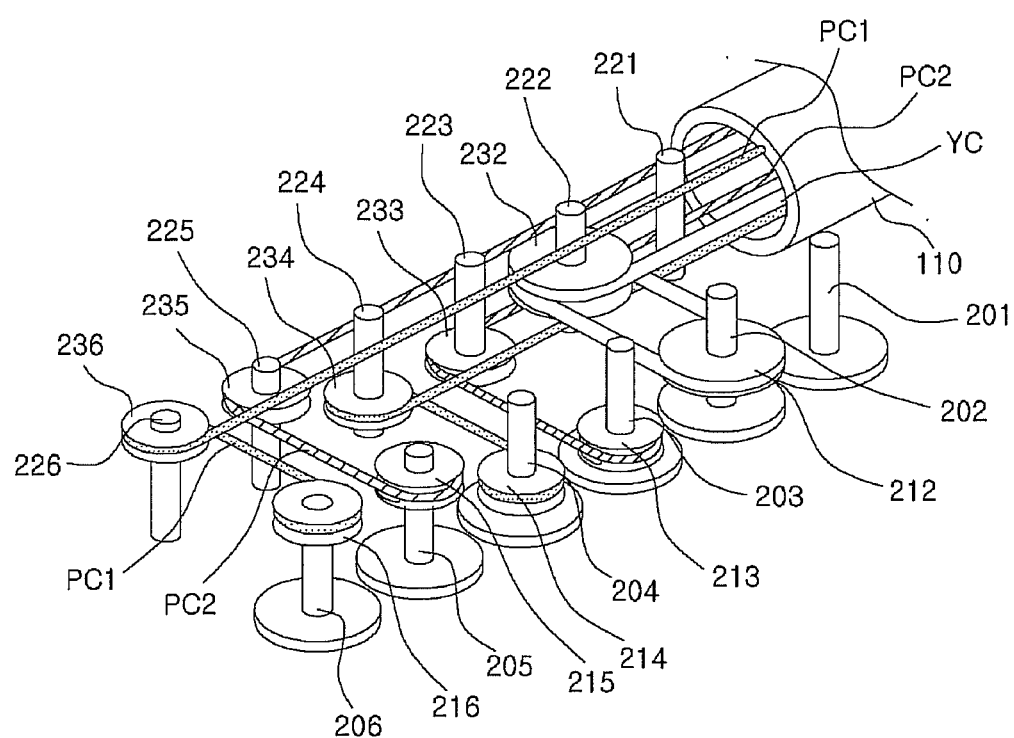

FIGS. 16 and 17 are perspective views showing the configuration of the handling part 200 in accordance with a first embodiment of the present invention, with the views seen from different directions. As illustrated in the drawings, first through sixth drive shafts 201-206 and first through sixth actuating shafts 221-226 are sequentially positioned opposedly to each other in parallel, and the second through sixth actuating shafts and the second through sixth actuating shafts, except for the first drive shaft and the first actuating shaft, are provided with second through sixth drive pulleys 212-216 and second through sixth actuating pulleys 232-236, respectively, to have cables wound around them, thereby letting them rotate around the shafts (where the pulley for each of the first shafts will be explained in another embodiment). Moreover, each of the drive shafts is connected to the corresponding drive roller 82 to receive a rotational motion therefrom. Meanwhile, the pulleys of the drive shafts or the actuating shafts are preferably positioned in different heights from each other to prevent interferences between the cables wound around the pulleys.

The drive pulleys and the actuating pulleys positioned opposedly from each other may have the same diameter to have the same drive range and the same actuating range, but they may also be given different diameters to have different drive ranges and different actuating ranges from each other. Besides, the drive pulleys and the actuating pulleys may have a proper width, taking the width of cables wound around each of them into consideration.

The following is a further explanation about an example of how yaw cable YC and the first and second pitch cables PC1 and PC2 are connected to the drive pulleys and the actuating pulleys of the handling part 200.

The second actuating pulley 232 is connected to the first yaw actuating part 112 by the yaw cable YC, so that the first actuating shaft 120 is controlled to operate in a yaw direction according to the rotation of the second actuating pulley 232. Since the second actuating pulley 232 is also connected to the second drive pulley 212 by another cable, it can receive a rotational motion from the second drive pulley 212.

The third actuating pulley 233 is connected to the first yaw actuating part 112, to the second yaw actuating part 122, and to the pitch actuating part 132 by the second pitch cable PC2. Since the third actuating pulley 233 is also connected to the third drive pulley 213 by the second pitch cable PC2, it can receive a rotational motion from the third drive pulley 213. One end of the second pitch cable PC2 can be secured to the third drive pulley 213. The other end of the second pitch cable PC2 can be connected to the fifth drive pulley 215 through the fifth actuating pulley 235.

Meanwhile, the fourth actuating pulley 234 is connected to the first yaw actuating part 112, to the second yaw actuating part 122 and to the pitch actuating part 132 by the first pitch cable PC1. Since the fourth actuating pulley 234 is also connected to the fourth drive pulley 214 by means of the first pitch cable PC1, it can receive a rotational motion from the fourth drive pulley 214. One end of the first pitch cables PC1 can be secured to the fourth drive pulley 214. The other end of the first pitch cable PC1 can be connected to the sixth drive pulley 216 via the sixth actuating pulley 236.

The following is a detailed explanation about the operations of the first and second actuating shafts 120 and 130 and the end effector 140 by the handling part 200 having the cable connections described above.

First, a yaw-wise rightward rotation mechanism of the first actuating shaft 120 with respect to the main shaft 110 will now be explained below.

When the second drive pulley 212 rotates clockwise, its rotational motion is transmitted to a yaw cable pulley (not shown) of the first yaw actuating part 112, and when the yaw cable pulley rotates accordingly, the first actuating shaft 120 rotates yaw-wise rightward.

At this time, the third and fifth drive pulleys 213 and 215 make the second pitch cable PC2 rotate in an unwind direction from the handling part 200, and the fourth and sixth drive pulleys 214 and 216 make the first pitch cable PC1 rotate in a pull direction towards the handling part 200. Thus, the second actuating shaft 130 may remain in a consistent position with respect to the first actuating shaft 120.

Now, a yaw-wise leftward rotation mechanism of the second actuating shaft 130 with respect to the first actuating shaft 120 will be explained below.

First, a yaw cable pulley (not shown) of the first yaw actuating part 112 is not allowed to rotate by securing the second drive pulley 212. By doing so, the first actuating shaft 120 is not allowed to rotate, either. In this state, the third and fifth drive pulleys 213 and 215 rotate the second pitch cable PC2 in the pull direction towards the handling part 200, and the fourth and sixth drive pulleys 214 and 216 rotate the first pitch cable PC1 in the unwind direction from the handling part 200. Accordingly, the second actuating shaft 130 rotates yaw-wise leftward with respect to the first actuating shaft 120.

A downward pitch-wise rotation mechanism of the end effector 140 will now be explained below.

First, a yaw cable pulley (not shown) of the first yaw actuating part 112 is not allowed to rotate by securing the second drive pulley 212. By doing so, the first actuating shaft 120 is not allowed to rotate, either. In this state, the third and fourth drive pulleys 213 and 214 connected to the second and first pitch cables PC2 and PC1 rotate the second and first pitch cables PC2 and PC1 in the pull direction towards the handling part 200, and the fifth and sixth drive pulleys 215 and 216 rotate the second and first pitch cables PC2 and PC1 in the unwind direction from the handling part 200. By doing so, while the second actuating shaft 130 is immobilized, the end effector 140 connected to the first and second pitch cables PC1 and PC2 rotate in a way that its two rods face downward pitch-wise at the same time.

The description so far has been focused mainly on the operational example of the tool 100 for minimally invasive surgery illustrated in FIG. 15, but it is obvious to a person having ordinary skill in the art that the same principle mechanism explained above may also be realized in different operational examples from the operational example provided here.

Embodiment II

Figure 18:
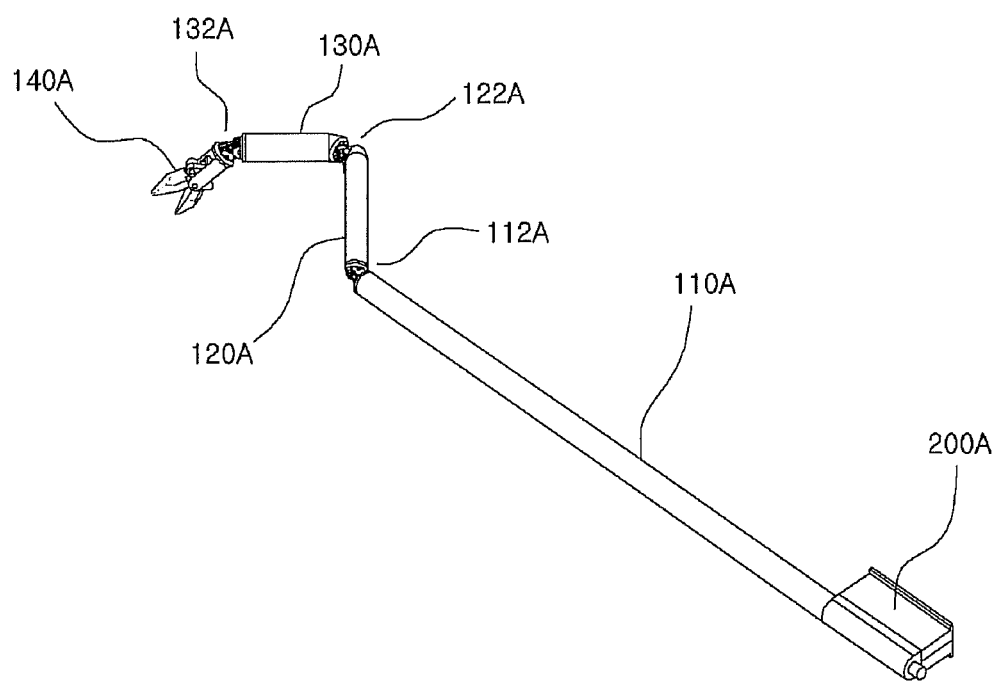
FIG. 18 is a perspective view showing another example of the tool for minimally invasive surgery used for the present invention.

FIG. 18 is a perspective view showing another example of a tool 100A for minimally invasive surgery used for the present invention.

The configuration of the tool 100A for minimally invasive surgery is basically similar to that of the tool 100 for minimally invasive surgery in accordance with the first embodiment, but an end effector 140A thereof is configured differently from the end effector 140 of the first embodiment. In addition, the tool 100A for minimally invasive surgery includes pitch cables PC, first and second yaw cables YC1 and YC2, and an opening/closing cable OC. Since more information on the configuration of this embodiment can be found in the first embodiment of the detailed description for the invention disclosed in Korean Patent Application No. 2008-79126, more details thereon will be omitted here.

The following is a detailed explanation about the configuration of a handling part 200A.

Figure 19:
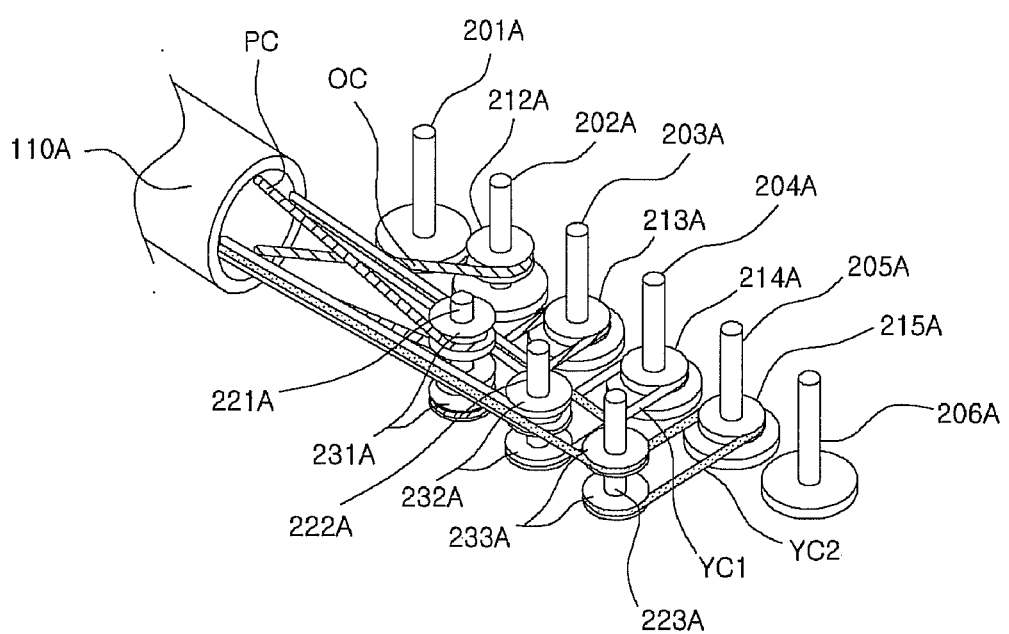
FIGS. 19 through 21 are perspective views showing the configuration of a handling part in accordance with a second embodiment of the present invention, with the views seen from different directions from each other.
Figure 20:
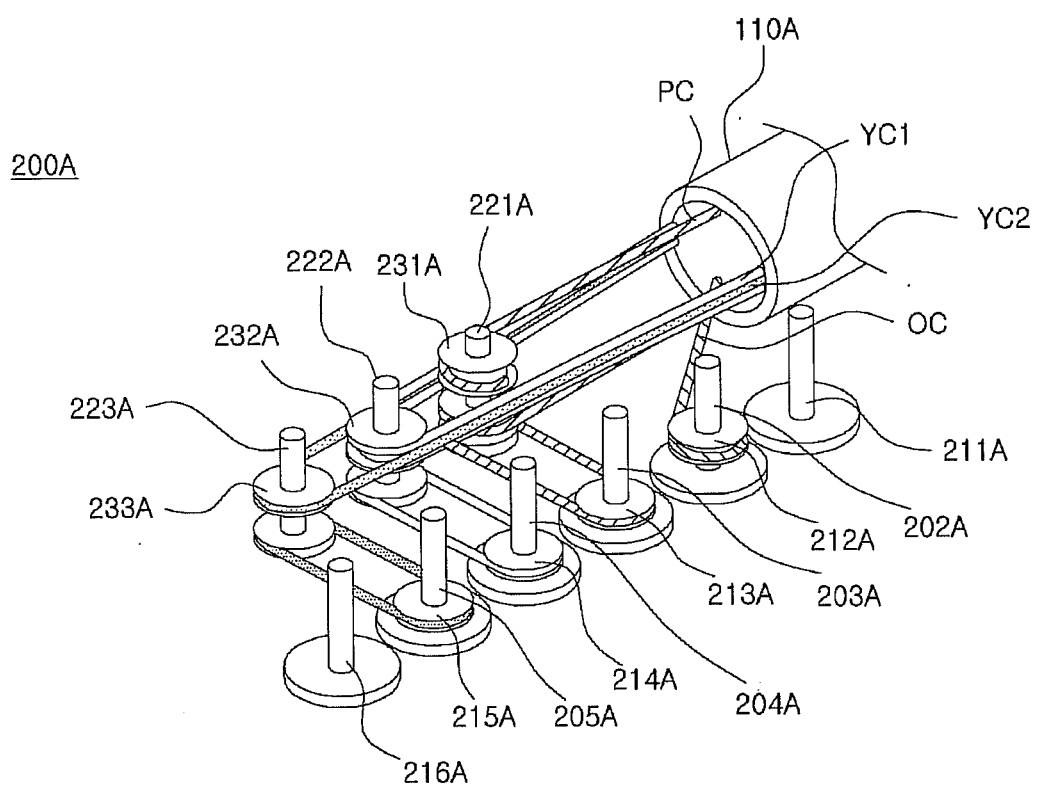
Figure 21:
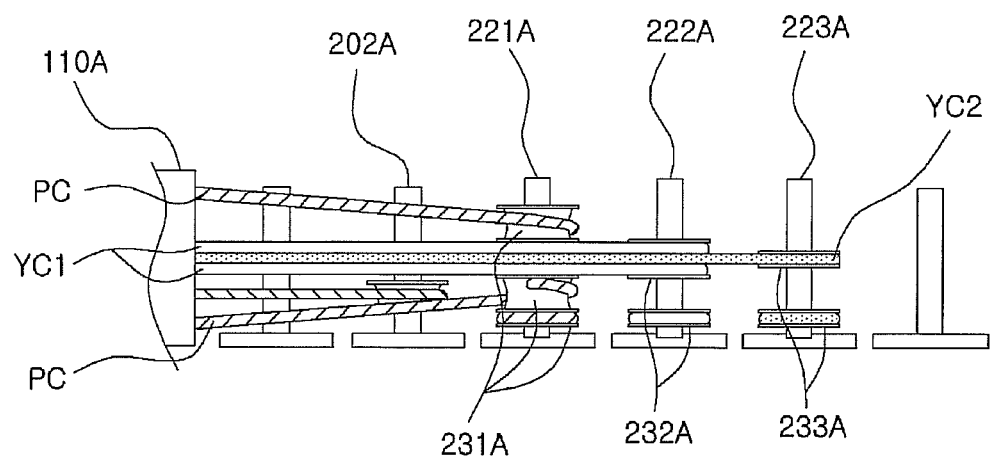

FIGS. 19 through 21 are perspective views showing the configuration of the handling part 200A in accordance with the second embodiment of the present invention, with the views seen from different directions from each other. As illustrated in the drawings, first through sixth drive shafts 201A-206A are positioned in parallel to first through third actuating shafts 221A-223A. Moreover, the first through third actuating shafts 221A-223A may be sequentially positioned opposedly from the third through fifth drive shafts 203A-205A. The drive shafts and the actuating shafts positioned opposedly from each other are provided with the third through fifth drive pulleys 213A-215A and the first through third actuating pulleys 231A-233A, respectively, thereby allowing the pulleys to rotate about the corresponding shafts. As noted in the previous embodiment, the drive rollers 82 can be connected to the drive shafts. This can be also equally applied to the embodiments to be described later.

Moreover, similar to the previous embodiment, the pulleys for the drive shafts or the actuating shafts may be positioned at different heights to prevent interferences between the cables wound around the pulleys.

Meanwhile, the drive pulleys and the actuating pulley may be given the same diameter or width, as those in the previously explained embodiment.

However, according to this embodiment, the first through third actuating pulleys 231A-233A each may be constituted with a pair of pulleys. The lower pulley in the actuating pulley pair is a pulley for receiving a drive force from the drive shaft, and the upper pulley in the actuating pulley pair is a pulley for transferring the received drive force to the opposite side of the shaft 110A.

The following is a description about an example of how the opening/closing cable OC, the pitch cables PC, and the first and second yaw cables YC1 and YC2 are connected to the drive pulleys and the actuating pulleys in the handling part 200A.

As shown in the drawings, one end of the opening/closing cable OC is wound around the second drive pulley 212A and secured thereto. The other end of the opening/closing cable OC is connected to the end effector 140A, so if the opening/closing cable OC is pulled according to the rotation of the second drive pulley 212A, the end effector 140A is closed; if the opening/closing cable OC is released, the end effector 140A is open by the restoring force of its spring.

Meanwhile, the first actuating pulley 231A is connected to a pitch actuating part 132A by the pitch cables PC. The first actuating pulley 231A is also connected to a third drive pulley 213A by another cable, so it can receive a rotational motion from the third drive pulley 213A.

The upper pulley of the second actuating pulley pair 232A and the upper pulley of the third actuating pulley pair 233A are connected to the first yaw cable YC1 and to the second yaw cable YC2, respectively. The second and third actuating pulleys 232A and 233A can also be driven by fourth and fifth drive pulleys 214A and 215B.

The following is a detailed explanation about the operations of the first and second actuating shafts 120A and 130A and the end effector 140A by the handling part 200A having the cable connections described above.

First, a yaw-wise rightward rotation mechanism of the first actuating shaft 120A with respect to the main shaft 110A will be explained below.

With the second drive pulley 212A and the third drive pulley 213A wound around with the opening/closing cable OC and with the pitch cables PC, respectively, being immovably secured not to rotate in any direction, if the fourth drive pulley 214A and the fifth drive pulley 215A rotate clockwise, the first actuating pulley 231A and the second actuating pulley 232A wound around with the first and second yaw cables YC1 and YC2, respectively, pull the first and second yaw cables YC1 and YC2 on the right side towards the handling part 200A, and unwind the first and second yaw cables YC1 and YC2 on the left side from the handling part 200A, such that the first actuating shaft 120A rotates yaw-wise rightward.

Now, a yaw-wise leftward rotation mechanism of the second actuating shaft 130A with respect to the first actuating shaft 120A will be explained below.

With the second drive pulley 212A, the third drive pulley 213A and the fourth drive pulley 214A being immovably secured not to rotate in any direction, if the fifth drive pulley 215A rotates counterclockwise, the third actuating pulley 23A also rotates counterclockwise. As such, the second yaw cable YC2 on the left side of the third actuating pulley 233A is pulled towards the handling part 200A, and the second yaw cable YC2 on the right side is unwound from the handling part 200A. Accordingly, the second actuating shaft 130A rotates yaw-wise leftward with respect to the first actuating shaft 120A.

A downward pitch-wise rotation mechanism of the end effector 140A will now be explained below.

With the second drive pulley 212A, the fourth drive pulley 214A and the fifth drive pulley 215A being immovably secured not to rotate in any direction, if the third drive pulley 213A wound around with the pitch cable PC rotates clockwise, the lower pitch cable PC is pulled, while the upper pitch cable PC is unwound, such that the end effector 140A rotates downward pitch-wise.

The description so far has been focused mainly on the operational example of the tool 100A for minimally invasive surgery illustrated in FIG. 18, but it is obvious to a person having ordinary skill in the art that the same principle mechanism explained above can also be realized in different operational examples from the operational example provided here.

Embodiment III

Figure 22:
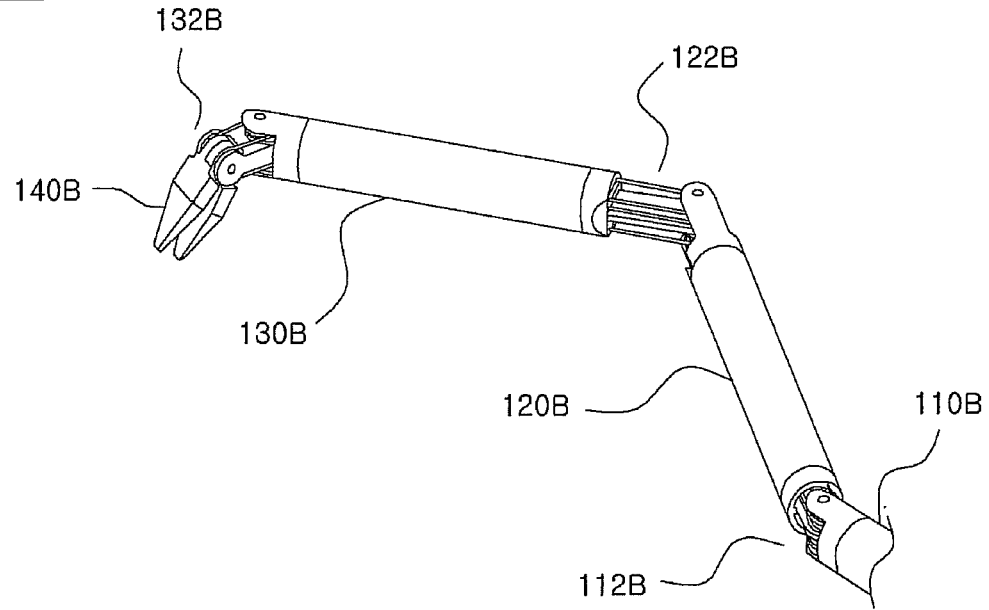
FIG. 22 is a perspective view showing still another example of the tool for minimally invasive surgery used for the present invention.

FIG. 22 is a perspective view showing another example of a tool 100B for minimally invasive surgery used for the present invention.

The configuration of the tool 100B for minimally invasive surgery is basically similar to that of the tools 100 and 100A for minimally invasive surgery in accordance with the previously explained embodiments, but it has a characteristic configuration for a connection part 132B connecting an end effector 140B to a second actuating shaft 130B. In addition, the tool 100B for minimally invasive surgery includes first and second pitch cables PC1 and PC2, and first and second yaw cables YC1 and YC2. Since more information on the configuration of this embodiment can be found in the fifth embodiment of the detailed description for the invention disclosed in Korean Patent Application No. 2008-90560, more details thereon will be omitted here.

The following is a description about the configuration of a handling part 200B.

Figure 23:
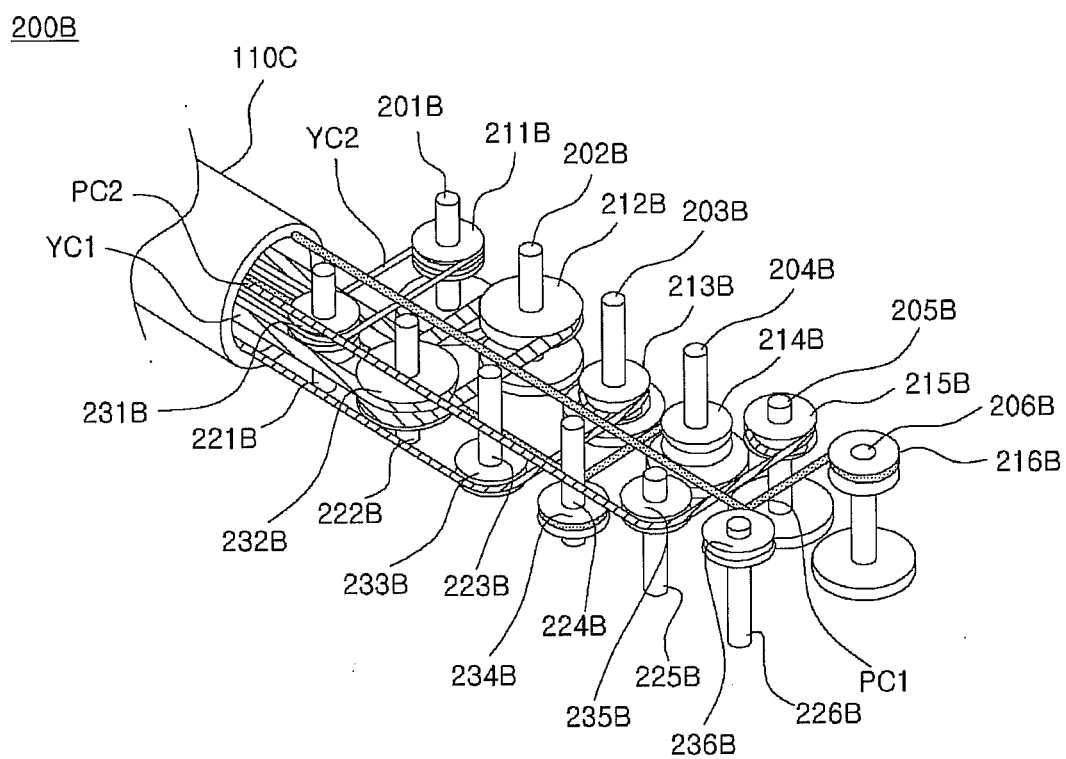
FIGS. 23 through 25 are perspective views showing the configuration of a handling part in accordance with a third embodiment of the present invention, with the views seen from different directions from each other.
Figure 24:
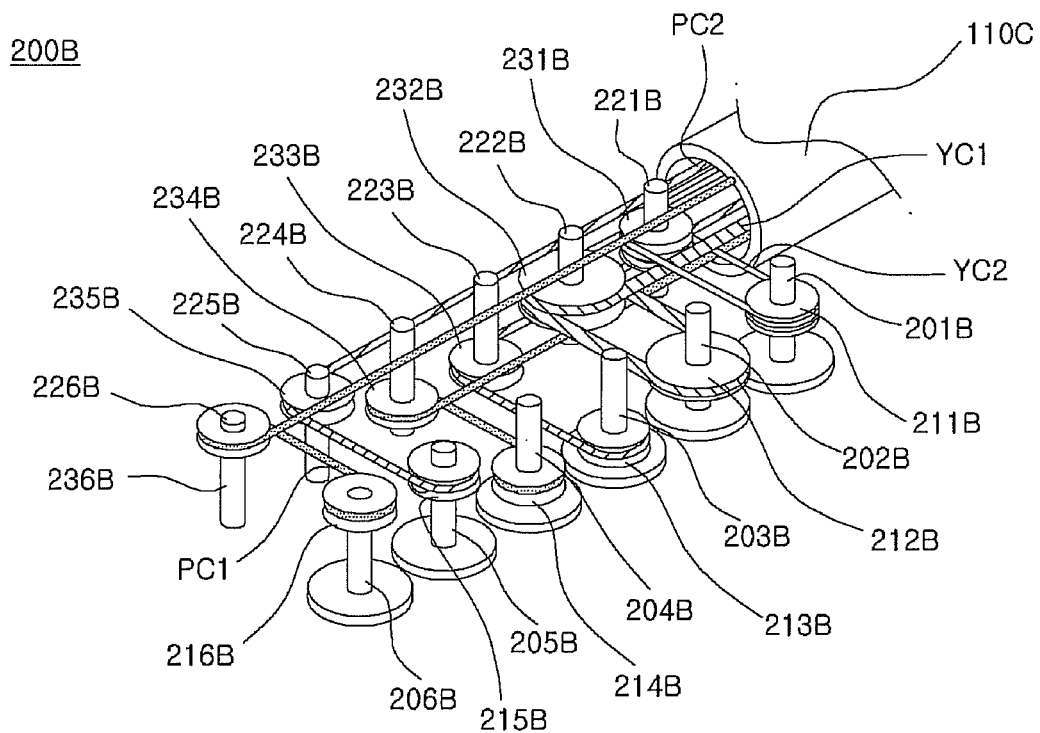
Figure 25:
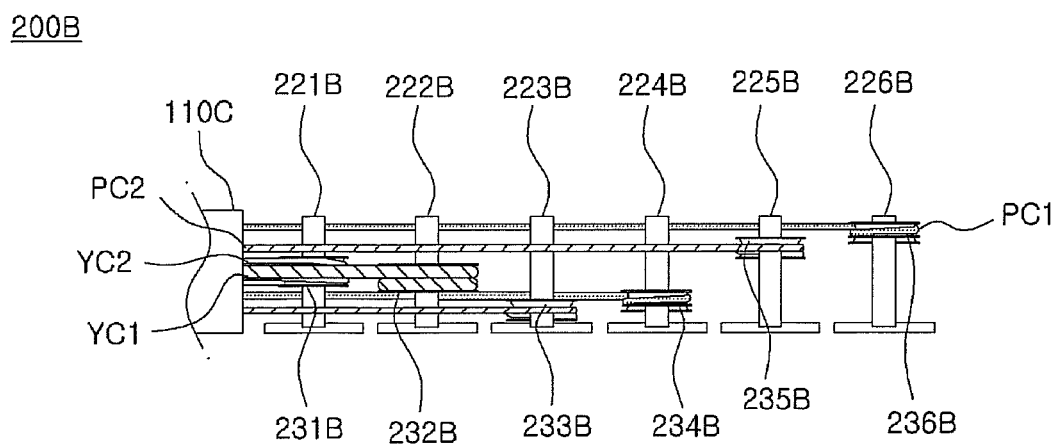

FIGS. 23 through 25 are perspective views showing the configuration of the handling part 200B in accordance with the third embodiment of the present invention, with the views seen from different directions from each other. As illustrated in the drawings, first through sixth drive shafts 201B-206B are sequentially positioned in parallel to first through sixth actuating shafts 221B-226B. As illustrated in the drawings, these shafts have drive pulleys and actuating pulleys having the similar functions and similar configuration features to those of the previously explained embodiments.

The following is an explanation about an example of how the first and second pitch cables PC1 and PC2 and the first and second yaw cables YC1 and YC2 are wound around the corresponding drive pulleys and actuating pulleys.

First, the second yaw cable YC2 being immovably secured to the first drive pulley 211B, winds around the first drive pulley 211B about twice in a loop form, and then the other end of each is immovably secured to the second yaw actuating part 122B via the first actuating pulley 231B. As the second yaw cable YC2 winds around the first drive pulley 211B twice, it causes no interference with the first yaw cable YC1. By the medium of the second cable YC2, the first actuating pulley 231B can control a yaw-wise operation of the second actuating shaft 130B.

Next, the first yaw cable YC1 connects the second actuating pulley 232B and the first yaw actuating pulley 112B to let the first actuating shaft 120 rotate in a yaw direction according to the rotation of the second actuating pulley 232B. At this time, the second actuating pulley 232B can also be driven by the second drive pulley 212B by the medium of another cable.

Meanwhile, the first and second pitch cables PC1 and PC2 have the same connections as those of the first and second pitch cables PC1 and PC2 in the first embodiment that was explained earlier with reference to FIGS. 16 and 17. The first and second pitch cables PC1 and PC2 can control the operations of the end effector 140B in the pitch and yaw directions by controlling the pitch-wise actuating joint and the yaw-wise actuating joint as explained in the fifth embodiment of the detailed description for the invention disclosed in Korean Patent Application No. 2008-90560.

The following is a detailed explanation about the operations of the first and second actuating shafts 120B and 130B and the end effector 140B by the handling part 200B having the cable connections described above.

First, a yaw-wise rightward rotation mechanism of the first actuating shaft 120B with respect to the main shaft 110B will now be explained below.

When the first and second drive pulleys 211B and 212B rotate clockwise, their rotational motions are transmitted to a yaw cable pulley (not shown) and a connection pulley (not shown) of the first yaw actuating part 112B, respectively, through the second and first yaw cables YC2 and YC1 wound around the first and second actuating pulleys 231B and 232B, so the first actuating shaft 120B rotates yaw-wise rightward. In this case, even though connection pulleys (not shown) positioned on both ends of a yaw cable pulley (not shown) of the first yaw actuating part 112B may rotate independently of the yaw cable pulley (not shown), in order to protect other elements from the influences of the operation of the first actuating shaft 120B, the third and fifth drive pulleys 213B and 215B rotate in the unwind direction of the second pitch cable PC2, while the fourth and sixth drive pulleys 214B and 216B rotate in the pull direction of the first pitch cable PC1.

Now, a yaw-wise leftward rotation mechanism of the second actuating shaft 130B with respect to the first actuating shaft 120B will be explained below.

First, a yaw cable pulley (not shown) is not allowed to rotate by securing the second drive pulley 212B. By doing so, the first actuating shaft 120B is not allowed to rotate, either.

In this state, if the first drive pulley 211B wound around the second yaw cable YC2 rotates counterclockwise, the second actuating shaft 130B where one end of the second yaw cable YC2 is wound around and secured to is pulled towards the handling part 200B.

Also, the third and fifth drive pulleys 213B and 215B wound around with the second pitch cable PC2 rotate to let the second pitch cable PC2 pulled towards the handling part 200B, and the fourth and sixth drive pulleys 214B and 216B rotate to let the first pitch cable PC1 rotate in the unwind direction from the handling part 200B. By doing so, the second actuating shaft 130B rotates yaw-wise leftward with respect to the first actuating shaft 120B.

A yaw-wise leftward rotation mechanism of the end effector 140B with respect to the connection part 132B will now be explained below.

First, the second and first yaw cables YC2 and YC1 are not allowed to operate by securing the first and second drive pulleys 211B and 211B(212B; 검토요망 ).

In this state, the third and fifth drive pulleys 213B and 215B let the second pitch cable PC2 rotate in the pull direction towards the handling part 200B, and the fourth and sixth drive pulleys 214B and 216B let the first pitch cable PC1 rotate in the unwind direction from the handling part 200B.

Because the first and second actuating shafts 120B and 130B cannot rotate with the first and second yaw cables YC1 and YC2 being immovably secured, the end effector 140B can rotate yaw-wise leftward with respect to the connection part 132B by the operations of the first and second pitch cables PC1 and PC2.

Now, a downward pitch-wise rotation mechanism of the end effector 140B will be explained below.

First, the first actuating shaft 120B and the second actuating shaft 130B are not allowed to rotate by securing the first and second drive pulleys 211B and 212B.

The third and fourth drive pulleys 213B and 214B wound around with the second and first pitch cables PC2 and PC1 let the second and first pitch cables PC2 and PC1 rotate in the pull direction towards the handling part 200B, and the fifth and sixth drive pulleys 215B and 216B let the second and first pitch cables PC2 and PC1 rotate in the unwind direction from the handling part 200B. As such, the first and second actuating shafts 120B and 130B are in immovable state, and the end effector 140B connected with the first and second pitch cables PC1 and PC2 rotates downward pitch-wise, with its two rods facing downward at the same time.

The description so far has been focused mainly on the operational example of the tool 100B for minimally invasive surgery illustrated in FIG. 22, but it is obvious to a person having ordinary skill in the art that the same principle mechanism explained above can also be realized in different operational examples from the operational example provided here.

Embodiment IV

Figure 26:
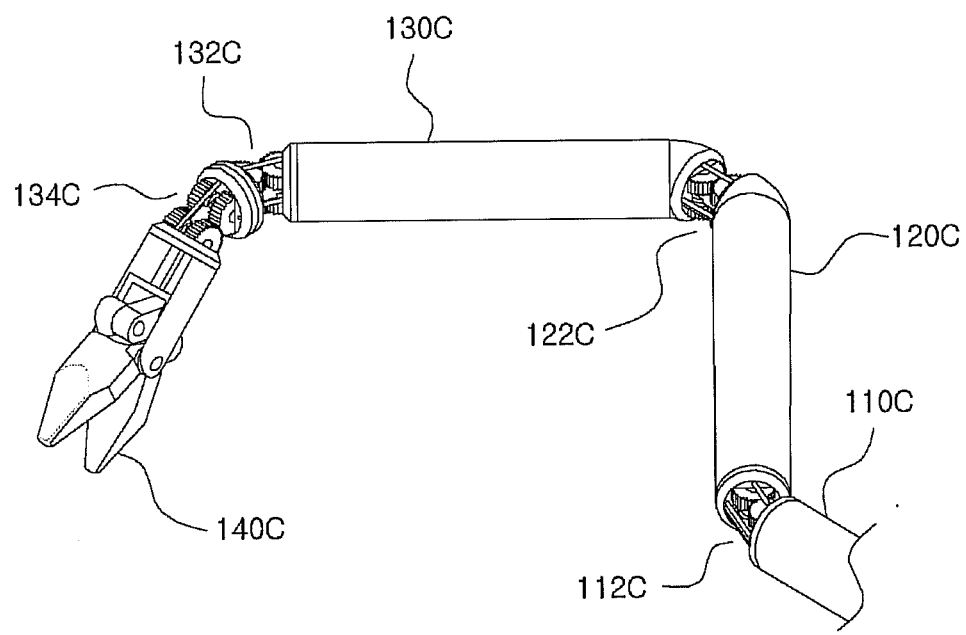
FIG. 26 is a perspective view showing still another example of the tool for minimally invasive surgery used for the present invention.

FIG. 26 is a perspective view showing still another example of a tool 100C for minimally invasive surgery used for the present invention.

The configuration of the tool 100C for minimally invasive surgery is basically similar to that of the tools 100, 100A and 100B for minimally invasive surgery in accordance with the previously explained embodiments, but it has a characteristic configuration for the third yaw actuating part 132C connecting an end effector 140C together with the pitch actuating part 134c to the second actuating shaft 130C. In addition, the tool 100C for minimally invasive surgery includes a pitch cable PC, first through third yaw cables YC1, YC2 and YC3, and an opening/closing cable OC. Since more information on the configuration of this embodiment can be found in the fourth embodiment of the detailed description for the invention disclosed in Korean Patent Application No. 2008-79126, more details thereon will be omitted here.

The following is a detailed explanation about the configuration of a handling part 200C.

Figure 27:
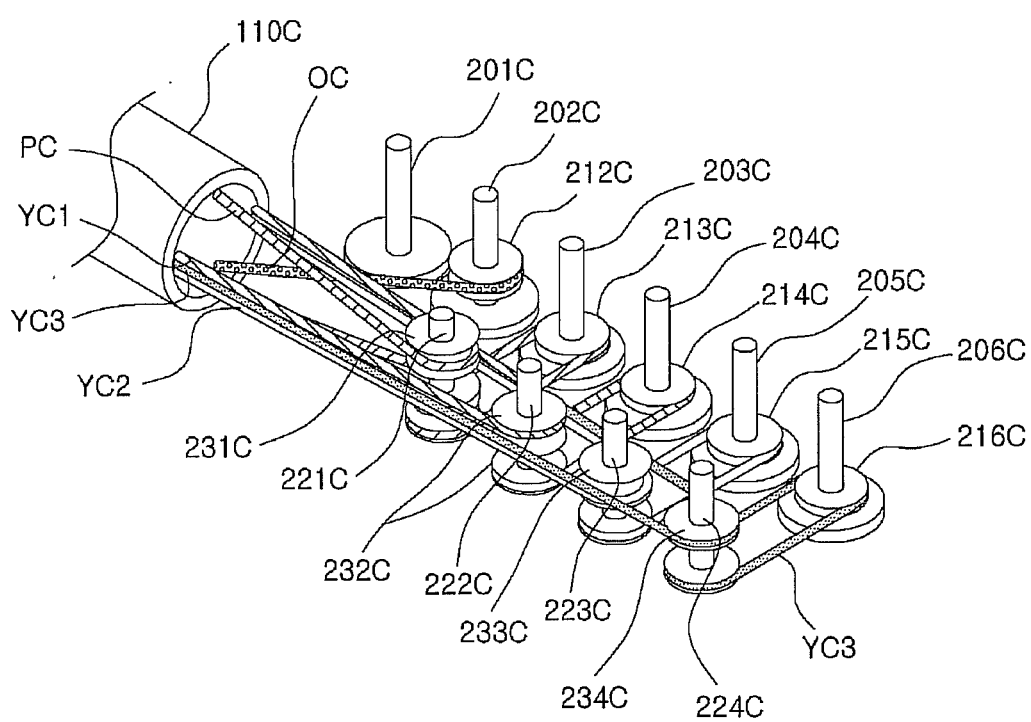
FIGS. 27 through 29 are perspective views showing the configuration of a handling part in accordance with a fourth embodiment of the present invention, with the views seen from different directions from each other.
Figure 28:
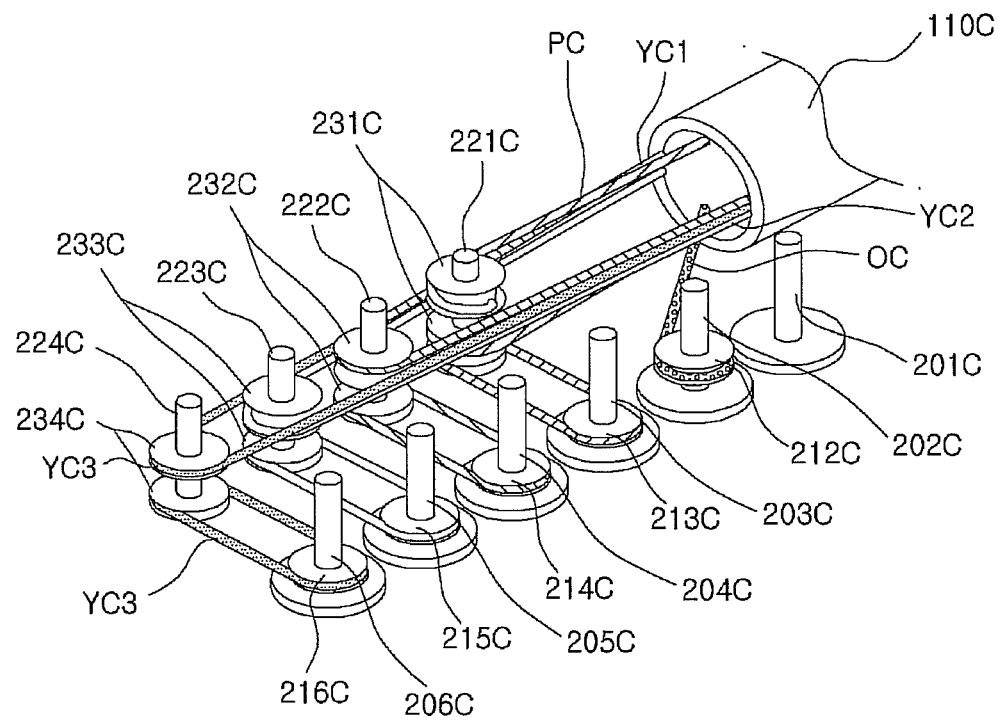
Figure 29:
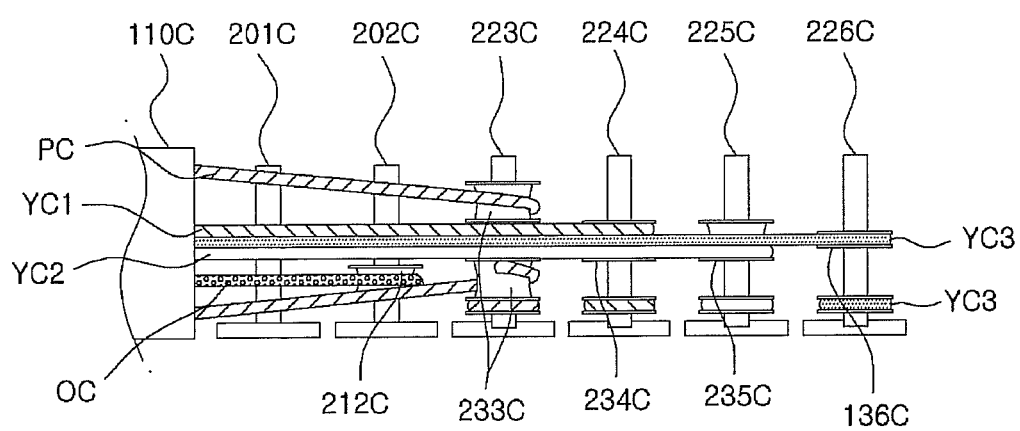

FIGS. 27 through 29 are perspective views showing the configuration of the handling part 200C in accordance with the fourth embodiment of the present invention, with the views seen from different directions from each other. As illustrated in the drawings, the positions and configurations of the first through sixth drive shafts 201C-206C and their corresponding first through third actuating shafts 221C-223C, and the positions and configurations of the third through fifth drive shafts 213C-215C and their corresponding first through third actuating pulleys 231C-233C are similar to those in the second embodiment explained previously.

Meanwhile, this embodiment differs from the second embodiment in that the fourth actuating shaft 224C is positioned oppositely from the sixth actuating shaft 206C, and the fourth actuating pulley 234C is positioned at the fourth actuating shaft 224C, thereby being driven together by the sixth drive pulley 216C.

The fourth actuating pulley 234C set forth above drives the third yaw actuating part 132C through the third yaw cable YC3 to let the operation of the end effector 140C controlled more in the yaw direction.

Embodiment V

Figure 30:
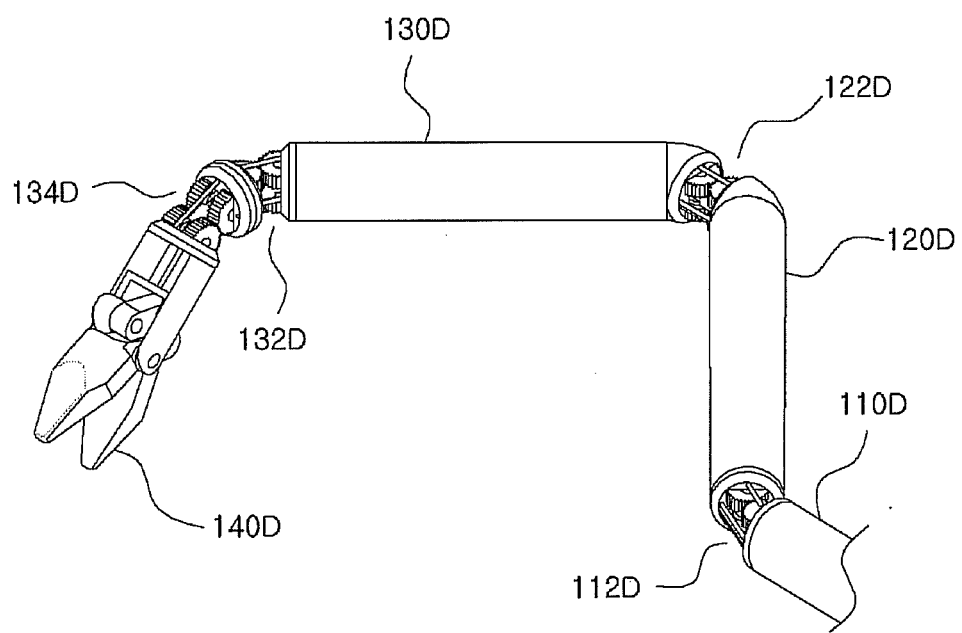
FIG. 30 is a perspective view showing still another example of the tool for minimally invasive surgery used for the present invention.

FIG. 30 is a perspective view showing still another example of a tool 100D for minimally invasive surgery used for the present invention.

The configuration of the tool 100D for minimally invasive surgery is basically similar to that of the tools 100, 100A, 100B and 100C for minimally invasive surgery in accordance with the previously explained embodiments, but it has a characteristic configuration for how the first and second yaw cables YC1 and YC2 are wound around their corresponding actuation pulleys 233D and 232D. Since more information on the configuration of this embodiment can be found in the fifth embodiment of the detailed description for the invention disclosed in Korean Patent Application No. 2008-79126, more details will be omitted here.

Figure 31:
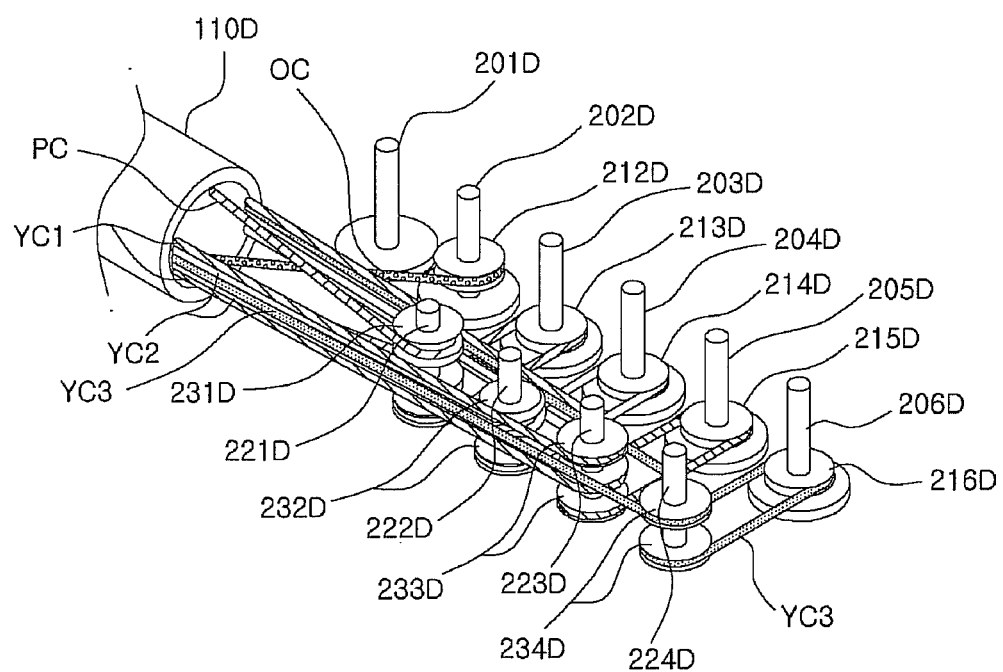
FIGS. 31 through 33 are perspective views showing the configuration of a handling part in accordance with a fifth embodiment of the present invention, with the views seen from different directions from each other.
Figure 32:
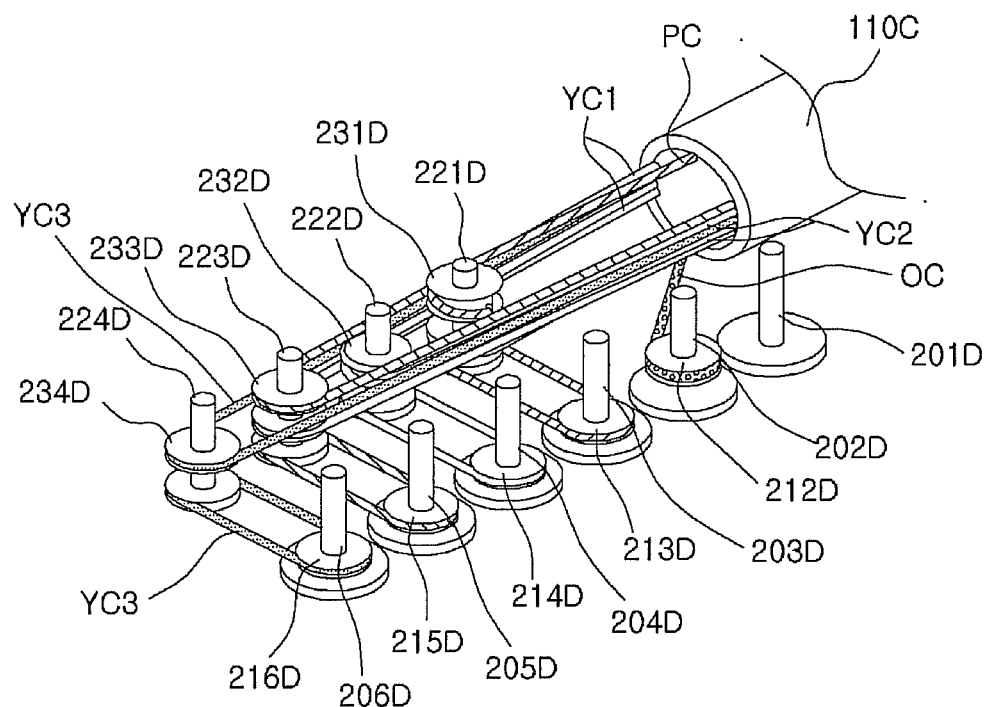
Figure 33:
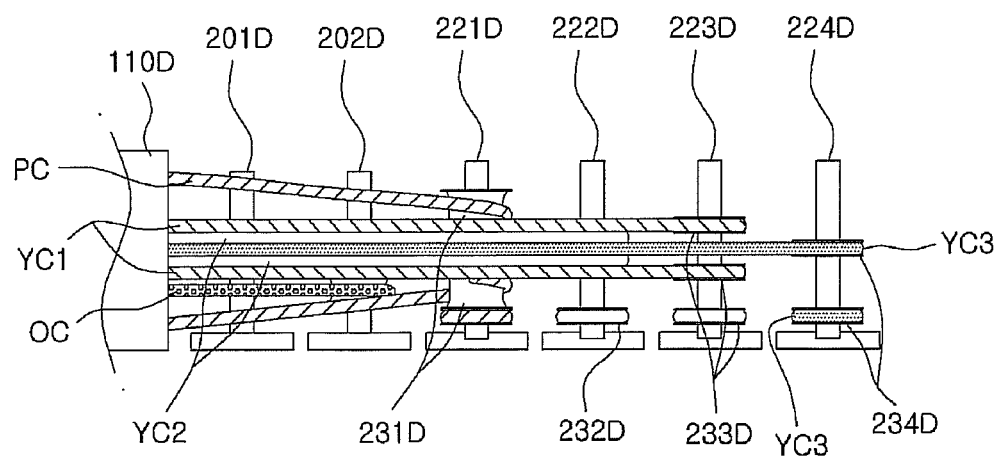

To see an example of how the first and second yaw cables YC1 and YC2 are wound around in the handling part 200D with reference to FIGS. 31 through 33 (especially, FIG. 33), the third actuating pulley 233D and the second actuating pulley 232D where the first and second yaw cables YC1 and YC2 are wound around, respectively, are double in-line pulleys or dual pulleys, so the first and second yaw cables YC1 and YC2 are wound around both sides about the third yaw cable YC3.

Embodiment VI

Figure 34:
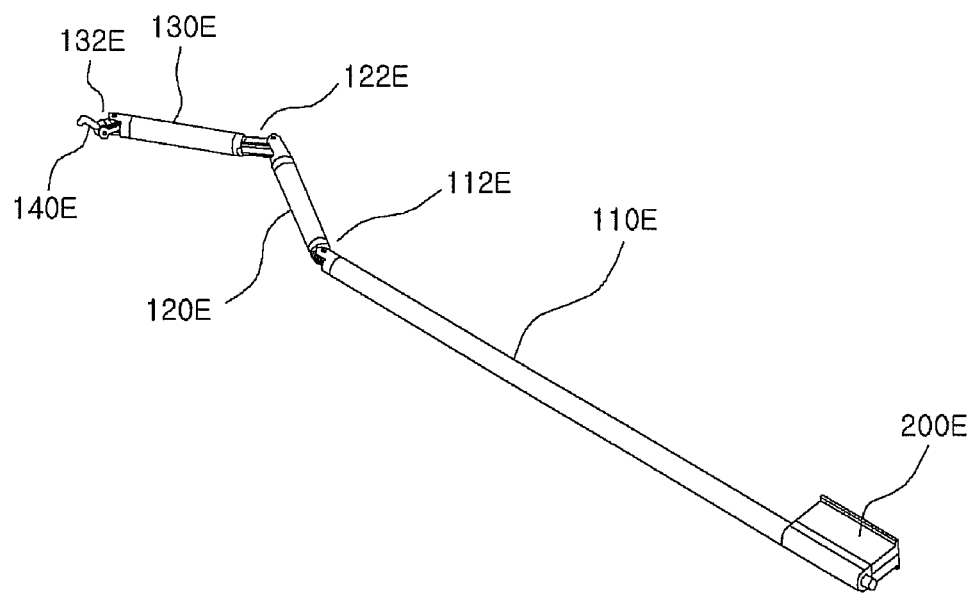
FIG. 34 is a perspective view showing still another example of the tool for minimally invasive surgery used for the present invention.

FIG. 34 is a perspective view showing still another example of a tool 100E for minimally invasive surgery used for the present invention. The configuration of this embodiment is identical to that of the third embodiment, except that a non-openable hook electrode has been utilized for the end effector 140E. In fact, the end effector 140E may take a variety of forms depending on the user's needs as long as it would not open or close.

Figure 35:
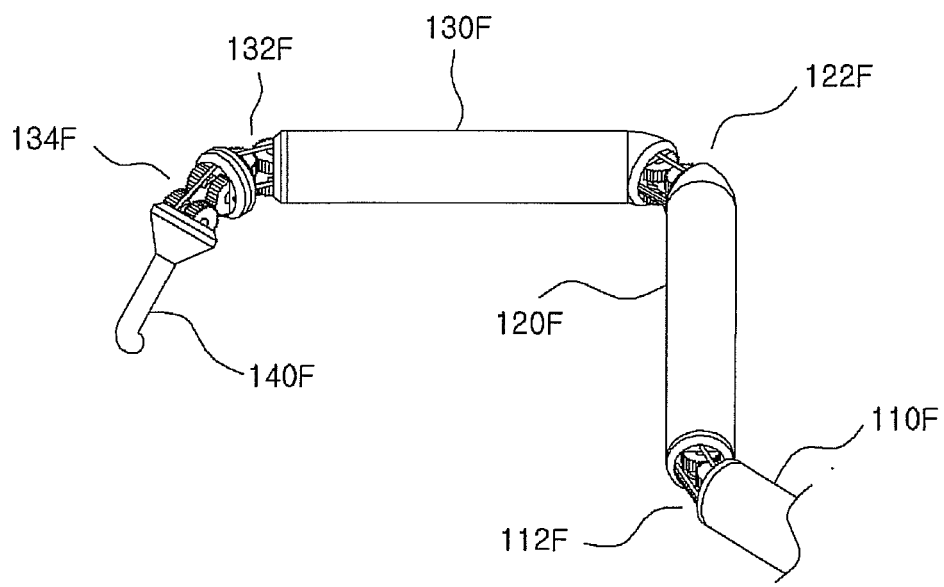
FIG. 35 is a perspective view showing still another example of the tool for minimally invasive surgery used for the present invention.

FIG. 35 is a perspective view showing still another example of a tool 100F for minimally invasive surgery used for the present invention. The configuration of this embodiment is identical to that of the fifth embodiment, except that an opening/closing cable is eliminated because a non-openable hook electrode has been utilized for the end effector 140F.

Configuration of Main Control Part

Figure 36:
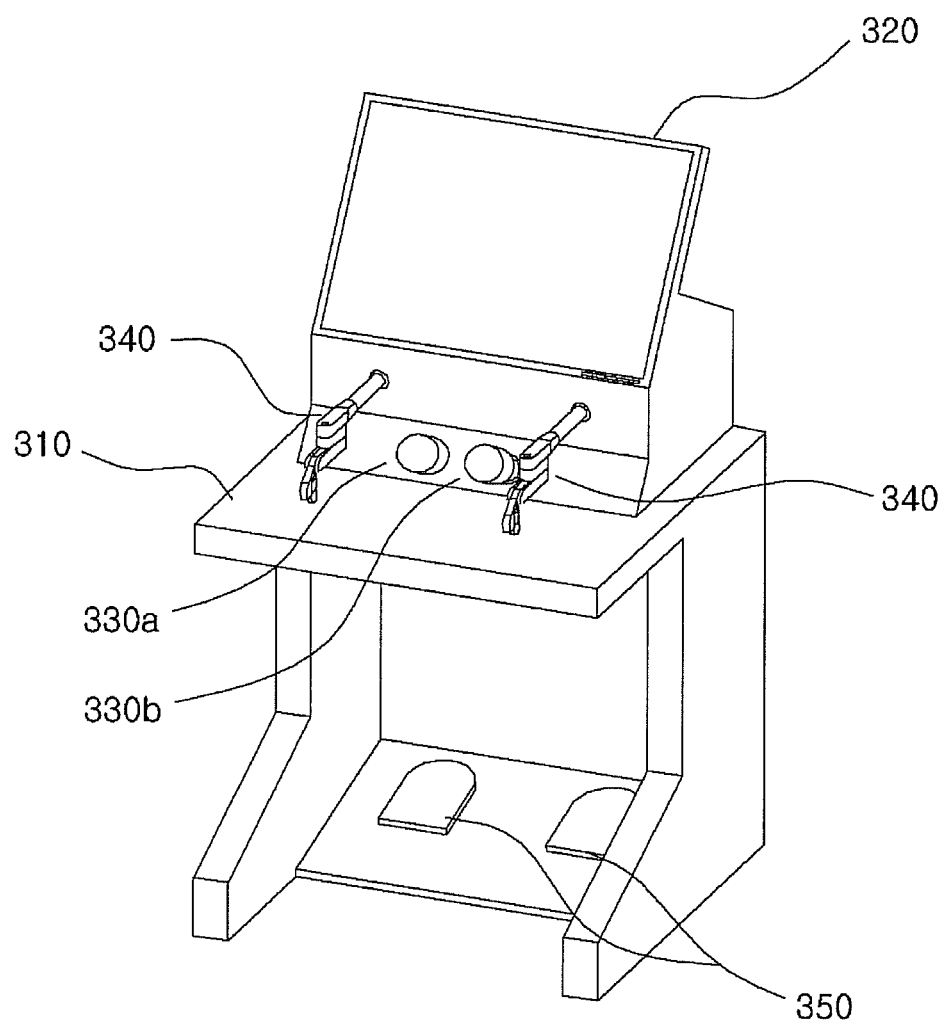
FIG. 36 is a perspective view showing the configuration of a main control part used for controlling the handling part of the tool for minimally invasive surgery used in embodiments in accordance with the present invention.

FIG. 36 is a perspective view showing the configuration of a main control part 300 used for controlling the handling part 200 of the tool 100 for minimally invasive surgery used in embodiments in accordance with the present invention. As shown in the drawing, the main control part 300 includes a table 310 having a predetermined height, a monitor 320 for displaying an image captured by an endoscope 50, a first joystick 330a for controlling the operation of the endoscope, a second joystick 330b for controlling the position of the surgery actuator 40 by controlling the operation of the robot arm 30, a pair of adjusting levers 340 for controlling the operation of the tool 100 for minimally invasive surgery, and a pair of pedals 350 for regulating predetermined operations of the tool 100 for minimally invasive surgery. This configuration is provided for illustrative purpose only, and the main control part 300 may take a variety of modified configurations, as long as it allows the user to operate the robot arm 30, the surgery actuator 40, the endoscope 50 positioned at the surgery actuator 40 and the tool 100 for minimally invasive surgery according to the user's intention.

Hereinafter, the operation control by the first joystick 330a, the second joystick 330b and the adjusting levers 340 will be explained with reference to drawings.

Figure 37:
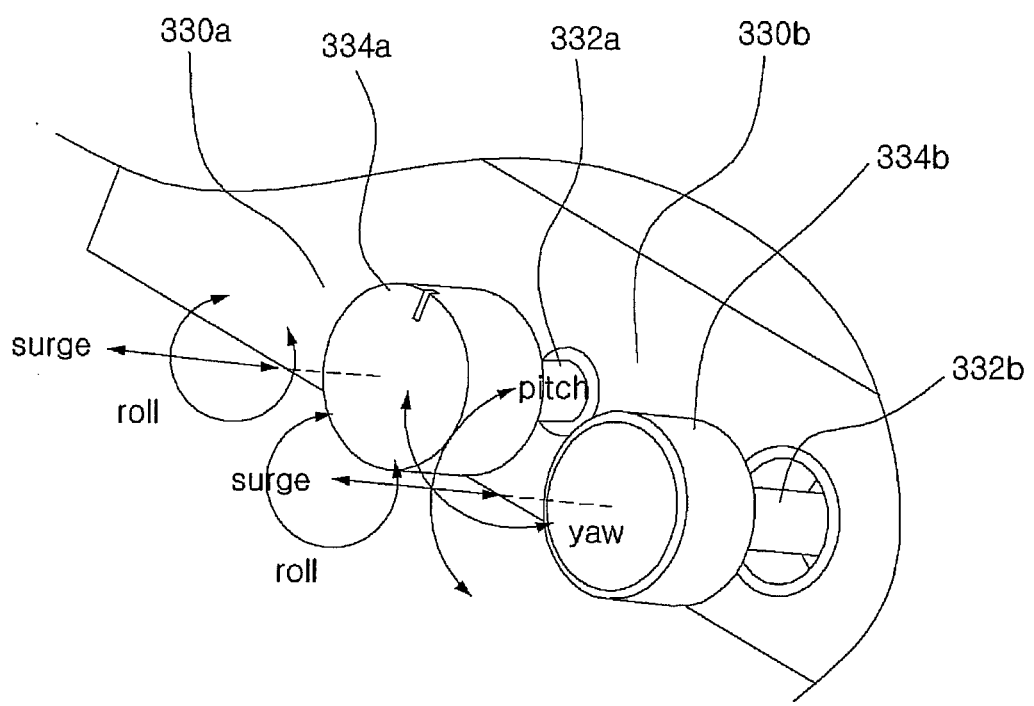
FIG. 37 shows actuation directions of first and second joysticks of the main control part in accordance with the present invention.
Figure 38:
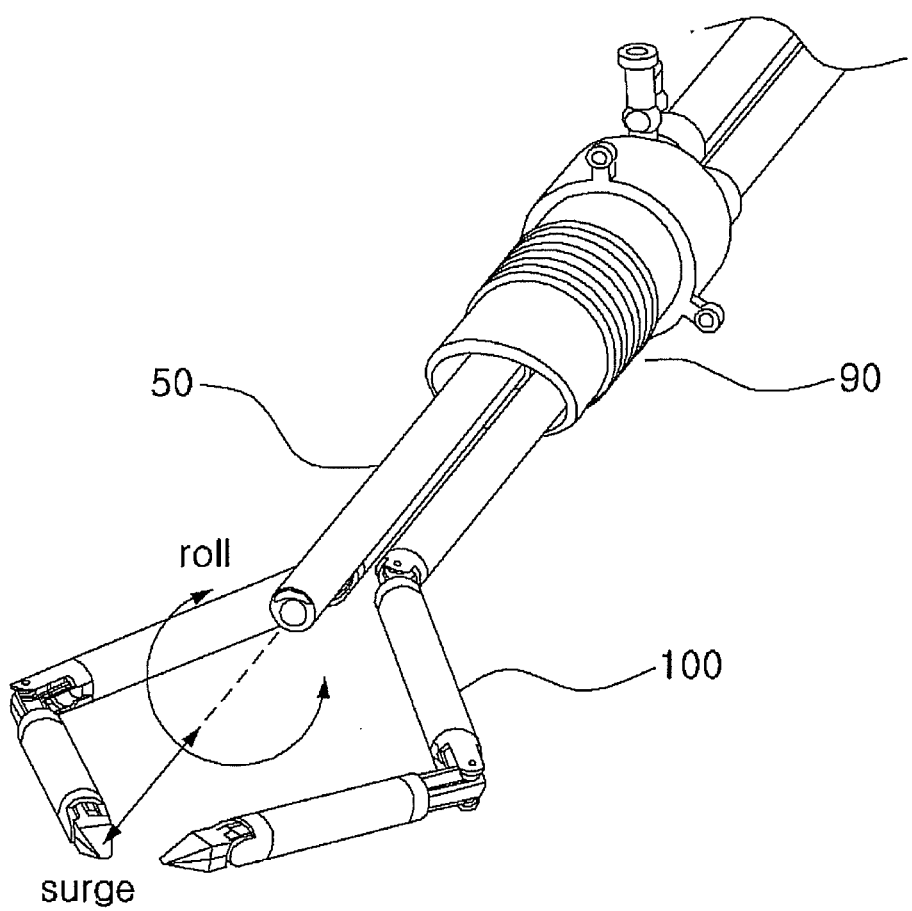
FIG. 38 shows actuation directions of an endoscope which is driven by the first joystick of the main control part in accordance with the present invention.
Figure 39:
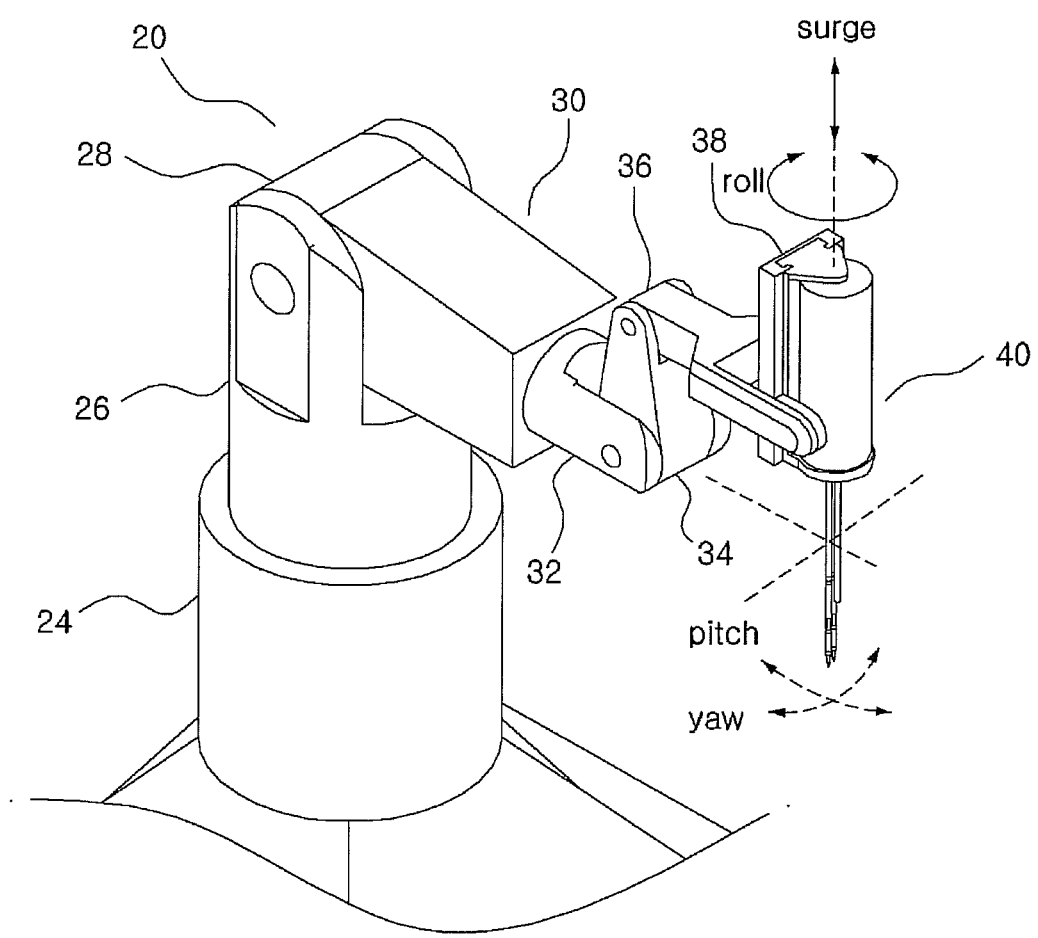
FIG. 39 shows actuation directions of the surgery actuator by a robot arm which is driven by the second joystick of the main control part in accordance with the present invention.

FIG. 37 shows actuation directions of the first and second joysticks 330a and 330b, FIG. 38 shows actuation directions of the endoscope 50 which is driven by the first joystick 330a, and FIG. 39 shows actuation directions of the surgery actuator 40 by the robot arm 30 which is driven by the second joystick 330b.

First, the configurations of the first and second joysticks 330a and 330b will be explained below.

As shown in the drawings, the first and second joysticks 330a and 330b are in form of dial type knobs 334a and 334b that are attached to the end of sticks 332a and 332b having a predetermined length, such that the first joystick 330a is allowed to handle the stick 332a in a surge direction and in a roll direction using the knob 334a and the second joystick 330b is allowed to handle the stick 332b in a surge direction, in a pitch direction, in a yaw direction and a roll direction using the knob 334b.

The following is an explanation about how the surgery actuator 40 and the endoscope 50 operate by the joysticks.

As illustrated in FIG. 37, the user can handle the second joystick 330b in a surge direction, in a pitch direction, in a yaw direction and/or in a roll direction, as he or she intended. That is to say, the user handles the second joystick 330b to drive the first through fourth robot arms 32, 34, 36 and 38 that constitute the robot arm 30, so as to control the surgery actuator 40 in a surge direction, in a pitch direction, in a yaw direction and/or in a roll direction, as illustrated in FIG. 39.

Also, the user can handle the first joystick 330a in a surge direction and in a roll direction. By handling the first joystick 330a, as illustrated in FIG. 38, the user can control the endoscope 50 in the surgery actuator 40 so that it operates in a surge direction and in a roll direction. However, it should be noted that if the first joystick 330a which is controllable only in the surge and roll directions is used, only a rigid endoscope having no articulation function can be used. Thus, in case of using an endoscope having an articulation function, it is preferable to handle the first joystick 330a, similar to the second joystick 330b, in a surge direction, in a pitch direction, in a yaw direction and/or in a roll direction.

Hereinafter, the operation control over the tool 100 for minimally invasive surgery by the adjusting lever 340 will be described with reference to drawings.

Because the adjusting lever 340 is for controlling the operation of the tool 100 for minimally invasive surgery, it will be helpful to use as many adjusting levers 340 as the tools 100 for minimally invasive surgery. That is, as illustrated in FIG. 36, a pair of (two) adjusting levers 340 can be utilized. However, if there are too many adjusting handles, the user is likely to feel confused during surgery. In such case, the user may use the pedals 350 to select a desired tool 100 for minimally invasive surgery controlled by the adjusting lever 340.

Figure 40:
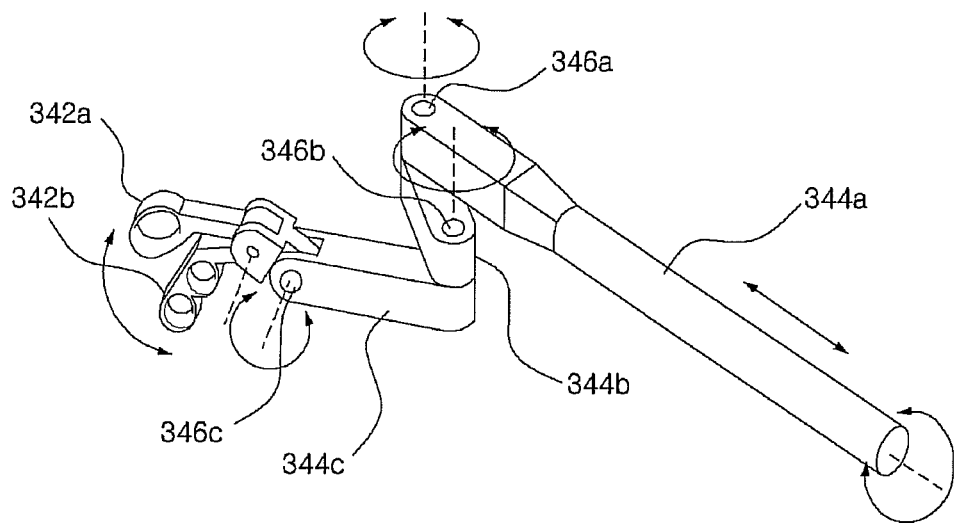
FIG. 40 shows actuation directions of an adjusting lever of the main control part in accordance with the present invention.

Referring now to FIG. 40, the adjusting lever 340 includes first, second and third handling rods 344a, 344b and 344c connected in sequence by first and second yaw rotational axes 346a and 346b. The first rod 342a and the second rod 342b, each having hole(s), are connected by a predetermined rotation axis, and they are again connected to one end of the third handling rod 344c by a pitch rotation axis 346c.

As the user handles the adjusting lever 340, the first and second rods 342a and 342b move in the pitch direction along the pitch rotation axis 346c, the first handling rod 344a operates in the surge direction and in the roll direction, and the second and third handling rods 344b and 344c operate in the yaw direction along the first and second yaw rotation axes 346a and 346b.

Meanwhile, if the tool 100 for minimally invasive surgery is openable/closeable, the user may open or close the end effector 140 by holding the first rod 342a and the second rod 342b and then increasing or decreasing an angular distance between them.

Figure 41:
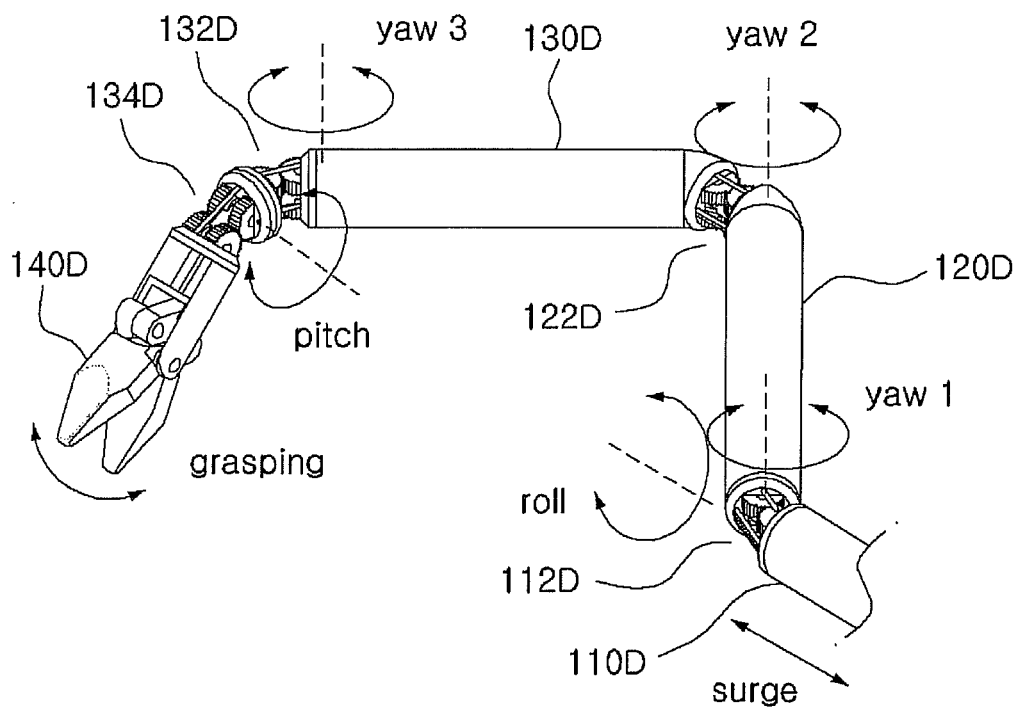
FIG. 41 shows actuation directions of a tool for minimally invasive surgery in accordance with a fifth embodiment of the present invention.

FIG. 41 shows an actuation direction of the tool 100D for minimally invasive surgery in accordance with the fifth embodiment of the present invention explained above. To explain the operation control by the adjusting lever 340 for example, when the first handling rod 344a of the adjusting lever 340 moves in the surge direction or in the roll direction, the shaft 110D operates corresponding to it. Also, the end effector 140D may operate in the pitch direction, or may be open/closed by handling the first rod 342a and the second rod 342b. Moreover, the first and second actuating shafts 120D and 130D may operate in the yaw directions yaw1 and yaw2 by handling the second and third handling rods 344b and 344c. In addition, if the adjusting lever 340 is configured to enable the first and second rods 342a and 342b to operate even in the yaw direction with respect to the third handling rod 344c, the rods may also operate in the yaw direction yaw3 of the end effector 140D illustrated in FIG. 41.

Whether to operate the rods, by handling the adjusting lever 340, in the yaw direction yaw1 or yaw2 of the first or second actuating shaft 120D or 130D or in the yaw direction yaw3 of the end effector 140D can be achieved by operating the pedals 350 (to be described later).

So far, the configuration and operation of the adjusting lever 340 have been discussed assuming that the lever is adapted to the first embodiment or the fifth embodiment of the tool for minimally invasive surgery of the present invention. However, it will be obvious to a person having ordinary skill in the art that modifications may be made to the adjusting lever 340 according to a corresponding tool for minimally invasive surgery without departing from the scope or principle applied to other embodiments of the present invention.

Lastly, the functions of the pedals 350 will be explained. As discussed earlier, the adjusting lever 340 includes three handling rods connected in sequence by two yaw-wise rotation joints, so the user should know, before making any choice, which yaw actuating part the yaw-wise rotation joints of his or her adjusting lever 340 belong to. That is, in case there are more than three yaw actuating parts or similar elements as in the third embodiment through the sixth embodiment, it would be better if the user knows which yaw actuating part or similar element the yaw-wise rotation joint of the adjusting lever 340 corresponds to and then takes suitable countermeasures in timely manner.

Figure 42:
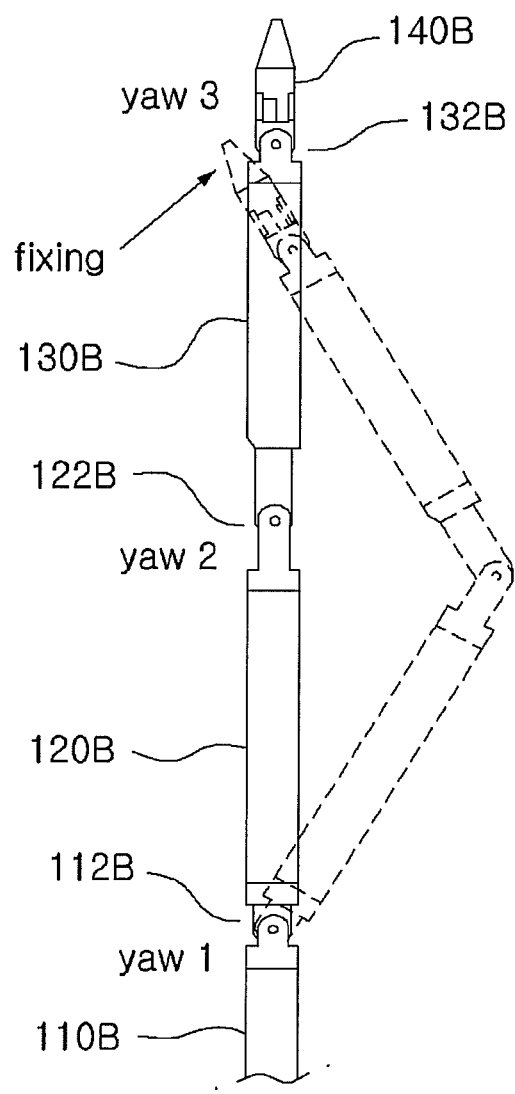
FIGS. 42 and 43 show actuation directions of a tool for minimally invasive surgery in response to pedal handling under the control of the main control part in accordance with the present invention.
Figure 43:
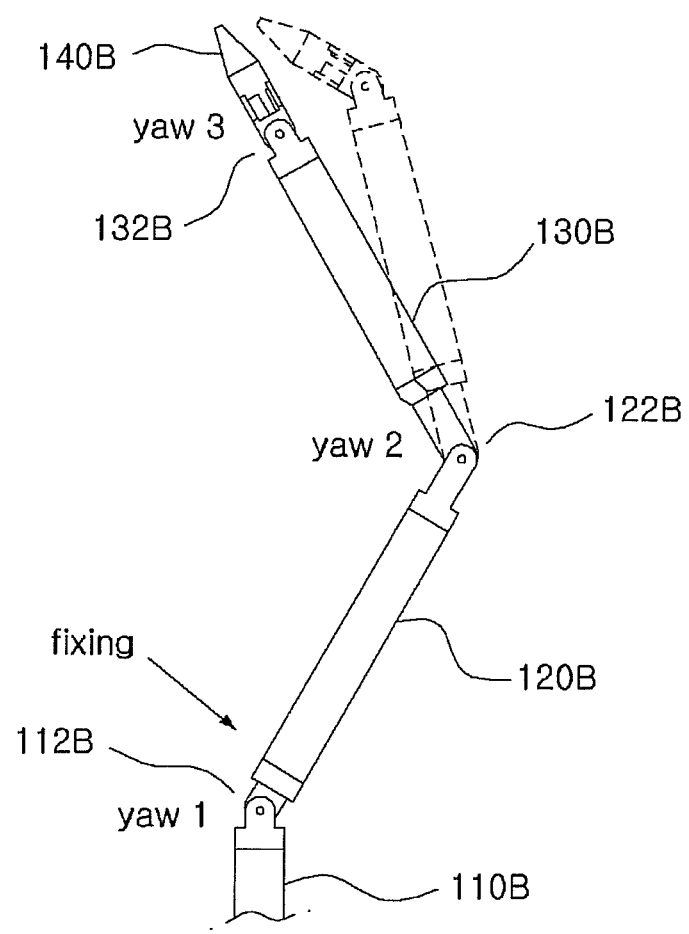

The above will be explained further with an illustration of FIGS. 42 and 43. Although the tool for minimally invasive surgery shown therein has a similar configuration to that of the tool 100B for minimally invasive surgery in accordance with the third embodiment, the present invention is not necessarily limited thereto.

First, the user steps on the pedals 350 to select a yaw actuating part corresponding to the rotation joint of the first or the second yaw rotation axis 346a, 346b. For instance, as illustrated in FIGS. 42 and 43, in the initial state (where the pedals 350 are not pressed, which corresponds to the left side view in FIGS. 42 and 43), rotation joints of the first and second yaw rotation axes 346a and 346b of the adjusting lever 340 correspond to the first and second yaw actuating parts 112B and 122B, respectively. On the other hand, with the user stepping on the pedals 350, rotation joints of the first and second yaw rotation axes 346a and 346b may correspond to the second yaw actuating part 122b and the connection part 132B, respectively (which corresponds to the right side view in FIGS. 42 and 43).

Needless to say, a person having ordinary skill in the art may use the pedals 350 differently from that explained in this embodiment. For example, if there are more yaw actuating parts, it may be possible to have a yaw actuating part corresponding to the rotation joint of the yaw rotation axis of the adjusting lever 340 be determined depending on the frequency for stepping on the pedals 350, or to simply operate the pedals 350 to determine which yaw actuating part the user needs to control without having to provide the adjusting lever 340 with more than two yaw rotation axes to do so.

Moreover, if there are more than three tools 100 for minimally invasive surgery positioned within the surgery actuator 40, it may also be possible for the user to select which tool 100 for minimally invasive surgery the adjusting levers 340 on both sides correspond to, based on the frequency for stepping on the pedals 350.

As described above, the present invention provides a surgical robot system suitable for use with a tool for carrying out a minimally invasive surgery in a dexterous and convenient manner.

In addition, the present invention presents a surgical robot system for enabling a user to perform remote surgery even if a patient to be operated on is far away in a physically different location.

Furthermore, the present invention suggests a surgical robot system for helping a user perform a minimally invasive surgery within a relatively short period of time using relatively low energy.

While the present invention has been described with respect to certain preferred embodiments, it will be apparent to a person having ordinary skill in the art that various changes and modifications may be made without departing from the scope of the invention as defined in the following claim.

What is claimed is:

1. A surgical robot system comprising,
a plurality of robot arms;
a surgery actuator, wherein the surgery actuator is controlled in a pitch direction and/or in a yaw direction by at least one of the plurality of robot arms, and
wherein the surgery actuator comprises at least one tool for minimally invasive surgery, and
wherein the at least one tool for minimally invasive surgery comprises a main shaft, a first actuating shaft, a second actuating shaft, an end effector and a handling part, and
wherein the handling part controls the first actuating shaft, the second actuating shaft and the end effector; and
a base, wherein the base comprises a vertical arm and a horizontal arm, and wherein the vertical arm operates in a surge direction and in a roll direction, and the horizontal arm operates in a pitch direction, and
wherein the surgery actuator is further controlled in a surge direction and/or in a roll direction by at least one of the plurality of robot arms, and
wherein the surgery actuator comprises at least two tools for minimally invasive surgery, and
wherein the at least two tools for minimally invasive surgery are positioned in parallel to each other, and
wherein the handling part comprises a plurality of drive pulleys, and
wherein each of the plurality of drive pulleys is driven by a drive roller, and
wherein the handling part further comprises a plurality of actuating pulleys, and
wherein each of the plurality of actuating pulleys is driven by at least one of the plurality of drive pulleys, and
wherein the plurality of actuating pulleys control the first actuating shaft, the second actuating shaft and/or the end effector, and
wherein the at least one tool for minimally invasive surgery further comprises a first yaw actuating part connecting the main shaft and the first actuating shaft, a second yaw actuating part connecting the first actuating shaft and the second actuating shaft, and a pitch actuating part connecting the second actuating shaft and the end effector, and
wherein the first yaw actuating part is connected to one of the plurality of actuating pulleys by a yaw cable, and
wherein the pitch actuating part, the first yaw actuating part and the second yaw actuating part are connected to the rest of the plurality of actuating pulleys by a first pitch cable and a second pitch cable.

2. The surgical robot system as claimed in claim 1, wherein the surgery actuator further comprises an endoscope.

3. The surgical robot system as claimed in claim 2, wherein the endoscope and the at least one tool for minimally invasive surgery form a bundle.

4. The surgical robot system as claimed in claim 2, wherein the endoscope and the at least one tool for minimally invasive surgery are controlled in a surge direction and/or in a roll direction to the surgery actuator, respectively.

5. The surgical robot system as claimed in claim 1, further comprising a main control part, wherein the main control part comprises at least one joystick and at least one adjusting lever, and
wherein the at least one joystick controls the surgery actuator, and the at least one adjusting lever controls the at least one tool for minimally invasive surgery.

6. The surgical robot system as claimed in claim 5, wherein the at least one joystick further controls an endoscope positioned at the surgery actuator.

7. The surgical robot system as claimed in claim 5, wherein at least one portion of the at least one joystick is handled in a surge direction, in a pitch direction, in a yaw direction and in a roll direction.

8. The surgical robot system as claimed in claim 5, wherein the at least one adjusting lever comprises a first handling rod, a second handling rod, a third handling rod, a first rod and a second rod,
wherein the first handling rod, the second handling rod and the third handling rod are connected in sequence by a first yaw rotation axis and a second yaw rotation axis,
wherein the third handling rod is connected to the first rod and the second rod by a pitch rotation axis, and wherein the motion of the first handling rod corresponds to that of the main shaft, the motion of the second handling rod corresponds to that of the first actuating shaft, the motion of the third handling rod corresponds to that of the second actuating shaft, and the motions of the first rod and the second rod correspond to those of the end effector.

9. The surgical robot system as claimed in claim 8, wherein the at least one tool for minimally invasive surgery further comprises a third actuating part or a connecting part connecting the second actuating shaft and the end effector,
wherein the main control part further comprises a pedal, and
wherein the motion corresponding relations between the handling rods and the shafts are variable according to handling the pedal.

10. The surgical robot system as claimed in claim 5, wherein the main control part further comprises a pedal, and
wherein the motion corresponding relation between the at least one adjusting lever and the at least one tool for minimally invasive surgery is variable.

11. A surgical robot system comprising,
a plurality of robot arms;
a surgery actuator, wherein the surgery actuator is controlled in a pitch direction and/or in a yaw direction by at least one of the plurality of robot arms, and
wherein the surgery actuator comprises at least one tool for minimally invasive surgery, and
wherein the at least one tool for minimally invasive surgery comprises a main shaft, a first actuating shaft, a second actuating shaft, an end effector and a handling part, and
wherein the handling part controls the first actuating shaft, the second actuating shaft and the end effector; and
a base, wherein the base comprises a vertical arm and a horizontal arm, and
wherein the vertical arm operates in a surge direction and in a roll direction, and the horizontal arm operates in a pitch direction, and
wherein the surgery actuator is further controlled in a surge direction and/or in a roll direction by at least one of the plurality of robot arms, and
wherein the surgery actuator comprises at least two tools for minimally invasive surgery,
wherein the at least two tools for minimally invasive surgery are positioned in parallel to each other, and
wherein the handling part comprises a plurality of drive pulleys, and
wherein each of the plurality of drive pulleys is driven by a drive roller, and
wherein the handling part further comprises a plurality of actuating pulleys, and
wherein each of the plurality of actuating pulleys is driven by at least one of the plurality of drive pulleys, and
wherein the plurality of actuating pulleys control the first actuating shaft, the second actuating shaft and/or the end effector, and
wherein the at least one tool for minimally invasive surgery further comprises a first yaw actuating part connecting the main shaft and the first actuating shaft, a second yaw actuating part connecting the first actuating shaft and the second actuating shaft, and a pitch actuating part connecting the second actuating shaft and the end effector, and
wherein the first yaw actuating part is connected to a first actuating pulley of the plurality of actuating pulleys by a first yaw cable, and
wherein the second yaw actuating part is connected to a second actuating pulley of the plurality of actuating pulleys by a second yaw cable, and
wherein the pitch actuating part is connected to a third actuating pulley of the plurality of actuating pulleys by a pitch cable, and
wherein the end effector is connected to a first drive pulley of the plurality of drive pulleys by an opening and closing cable.

12. The surgical robot system as claimed in claim 11, wherein the at least one tool for minimally invasive surgery further comprises a third yaw actuating part connecting the second actuating shaft and the end effector, and
wherein the third yaw actuating part is connected to a fourth actuating pulley of the plurality of actuating pulleys by a third yaw cable.

13. The surgical robot system as claimed in claim 11, wherein the surgery actuator further comprises an endoscope.

14. The surgical robot system as claimed in claim 13, wherein the endoscope and the at least one tool for minimally invasive surgery form a bundle.

15. The surgical robot system as claimed in claim 13, wherein the endoscope and the at least one tool for minimally invasive surgery are controlled in a surge direction and/or in a roll direction to the surgery actuator, respectively.

16. A surgical robot system comprising,
a plurality of robot arms;
a surgery actuator, wherein the surgery actuator is controlled in a pitch direction and/or in a yaw direction by at least one of the plurality of robot arms, and
wherein the surgery actuator comprises at least one tool for minimally invasive surgery, and
wherein the at least one tool for minimally invasive surgery comprises a main shaft, a first actuating shaft, a second actuating shaft, an end effector and a handling part, and
wherein the handling part controls the first actuating shaft, the second actuating shaft and the end effector; and
a base, wherein the base comprises a vertical arm and a horizontal arm, and
wherein the vertical arm operates in a surge direction and in a roll direction, and the horizontal arm operates in a pitch direction, and
wherein the surgery actuator is further controlled in a surge direction and/or in a roll direction by at least one of the plurality of robot arms, and
wherein the surgery actuator comprises at least two tools for minimally invasive surgery, and
wherein the at least two tools for minimally invasive surgery are positioned in parallel to each other, and
wherein the handling part comprises a plurality of drive pulleys, and
wherein each of the plurality of drive pulleys is driven by a drive roller, and
wherein the handling part further comprises a plurality of actuating pulleys, and
wherein each of the plurality of actuating pulleys is driven by at least one of the plurality of drive pulleys, and
wherein the plurality of actuating pulleys control the first actuating shaft, the second actuating shaft and/or the end effector, and
wherein the at least one tool for minimally invasive surgery further comprises a first yaw actuating part connecting the main shaft and the first actuating shaft, a second yaw actuating part connecting the first actuating shaft and the second actuating shaft, and a connecting part connecting the second actuating shaft and the end effector, and wherein the first yaw actuating part is connected to a first actuating pulley of the plurality of actuating pulleys by a first yaw cable, and wherein the second yaw actuating part is connected to a second actuating pulley of the plurality of actuating pulleys by a second yaw cable, and wherein the connecting part, the first yaw actuating part and the second yaw actuating part are connected to the rest of the plurality of actuating pulleys by a first pitch cable and a second pitch cable.

17. The surgical robot system as claimed in claim 16, wherein the surgery actuator further comprises an endoscope.

18. The surgical robot system as claimed in claim 17, wherein the endoscope and the at least one tool for minimally invasive surgery form a bundle.

19. The surgical robot system as claimed in claim 17, wherein the endoscope and the at least one tool for minimally invasive surgery are controlled in a surge direction and/or in a roll direction to the surgery actuator, respectively.

20. A surgical robot system comprising,
a plurality of robot arms;
a surgery actuator, wherein the surgery actuator is controlled in a pitch direction and/or in a yaw direction by at least one of the plurality of robot arms, and
wherein the surgery actuator comprises at least one tool for minimally invasive surgery, and
wherein the at least one tool for minimally invasive surgery comprises a main shaft, a first actuating shaft, a second actuating shaft, an end effector and a handling part, and
wherein the handling part controls the first actuating shaft, the second actuating shaft and the end effector; and
a base, wherein the base comprises a vertical arm and a horizontal arm, and
wherein the vertical arm operates in a surge direction and in a roll direction, and the horizontal arm operates in a pitch direction, and wherein the surgery actuator is further controlled in a surge direction and/or in a roll direction by at least one of the plurality of robot arms, and wherein the surgery actuator comprises at least two tools for minimally invasive surgery, wherein the at least two tools for minimally invasive surgery are positioned in parallel to each other, and wherein the handling part comprises a plurality of drive pulleys, and wherein each of the plurality of drive pulleys is driven by a drive roller, and wherein the handling part further comprises a plurality of actuating pulleys, and wherein each of the plurality of actuating pulleys is driven by at least one of the plurality of drive pulleys, and wherein the plurality of actuating pulleys control the first actuating shaft, the second actuating shaft and/or the end effector, and wherein the at least one tool for minimally invasive surgery further comprises a first yaw actuating part connecting the main shaft and the first actuating shaft, a second yaw actuating part connecting the first actuating shaft and the second actuating shaft, and a pitch actuating part connecting the second actuating shaft and the end effector, and wherein the first yaw actuating part is connected to a first actuating pulley of the plurality of actuating pulleys by a first yaw cable, and wherein the second yaw actuating part is connected to a second actuating pulley of the plurality of actuating pulleys by a second yaw cable, and wherein the pitch actuating part is connected to a third actuating pulley of the plurality of actuating pulleys by a pitch cable.

21. The surgical robot system as claimed in claim 20, wherein the surgery actuator further comprises an endoscope.

* * * * *